United States Patent [19]

Myers et al.

[11] Patent Number: 5,858,765
[45] Date of Patent: Jan. 12, 1999

[54] CONSTITUTIVE PSEUDOHYPHAL GROWTH YEAST MUTANTS

[75] Inventors: Alan M. Myers, Ames, Iowa; Pascal Madaule, Vauhallan, France

[73] Assignees: Iowa State University Research Foundation, Ames, Iowa; Institut Pasteur; Institut National de la Santé et de la Recherche Médicale, both of Paris, France

[21] Appl. No.: 61,636

[22] Filed: May 12, 1993

[51] Int. Cl.⁶ ............................. C12N 1/19; C12N 15/00; C12N 1/18

[52] U.S. Cl. .................................. 435/254.21; 435/172.3; 435/254.2

[58] Field of Search ........................ 536/20.7; 435/172.3, 435/254.2, 254.21, 255.2

[56] References Cited

FOREIGN PATENT DOCUMENTS

WO9308285  4/1993  WIPO.

OTHER PUBLICATIONS

J. Rine et al., "*Saccharomyces cerevisiae* as a Paradigm for Modern Molecular Genetics of fungi" in *Gene Manipulations in Fungi*; J.W. Bennet et al., Eds.; Academic Press: San Diego, CA; pp. 25–151; 1985.
J. Chant et al., "Genetic Control of Bud Site Selection in Yeast by a Set of Gene Products That Constitute a Morphogenetic Pathway, "*Cell*, 65, 1203–1212 (Jun. 28, 1991).
*Current Protocols in Molecular Biology*; F. Ausubel et al., Eds.; John Wiley and Sons: New York, NY (1989) —Title page, Copyright page, and Contents pages (pp. iii–x).
J. Devereux et al., "A comprehensive set of sequence analysis programs for the VAX," *Nucleic Acids Res.*, 12(1), 387–395 (1984).
D. Freifelder, "Bud Position in *Saccharomyces Cerevisiae*," *J. Bacteriol.*, 80, 567–568 (1960).
C.J. Gimeno et al., "Unipolar Cell Divisions in the Yeast S. Cerevisiae Lead to Filamentous Growth: Regulation by Starvation and *RAS*," *Cell*, 68, 1077–1090 (Mar. 20, 1992).
B. Goud et al., "A GTP–Binding Protein Required for Secretion Rapidly Associates with Secretory Vesicles and the Plasma Membrane in Yeast," *Cell*, 53, 753–768 (1988).
M. Grenson et al., "Multiplicity of the Amino Acid Permeases in *Saccharomyces Cerevisiae*," *Biochim. Biophys. Acta*, 127, 325–338 (1966).
S.K. Hanks et al., "The Protein Kinase Family: Conserved Features and Deduced Phylogeny of the Catalytic Domains," *Science*, 241, 42–51 (Jul. 1, 1988).
L.H. Hartwell, "Genetic Control of the Cell Division Cycle in Yeast, IV. Genes Controlling Bud Emergence and Cytokinesis," *Exptl. Cell Res.*, 69 265–276 (1971).
A.M. Healy et al., "CDC55, a *Saccharomyces cerevisiae* Gene Involved in Cellular Morphogenesis: Identification, Characterization, and Homology to the B Subunit of Mammalian Type 2A Protein Phosphatase," *Mol. Cell. Biol.*, 11(11), 5767–5780 (Nov. 1991).

J.E. Hill et al., "Yeast/*E. coli* Shuttle Vectors with Multiple Unique Restriction Sites," *Yeast*, 2, 163–167 (1986).
A.T. Locrincz et al., "Primary structure homology between the product of yeast cell division control gene *CDC28*and vertebrate oncogenes," *Nature*, 307 183–185 (Jan. 12, 1984).
M. Rose, et a., "Structure and function of the yeast *URA3*gene: expression in *Escherichia coli*," *Gene*, 29, 113–124 (1984).
R. Rothstein, "Targeting, Disruption, Replacement, and Allele Rescue: Integrative DNA Transformation in Yeast," *Meth. Enzymol.*, 194 281–301 (1991).
J. Sambrook et al., *Molecular Cloning, A Laboratory Manual,* Cold Spring Harber Laboratory: Cold Spring Harbor, NY (1989) —Title page, Copyright page, and Contents pages (pp. v–xxxii).
F. Sherman et al., Laboratory Course Manual for Methods in Yeast *Genetics,* Cold Spring Harbor Laboratory: Cold Spring Harbor, NY (1986) —Title page, Copyright page, and Contents pages.
A.H. Siddiqui et al., "A Regulatory Region Responsible for Proline–Specific Induction of the Yeast *PUT2* Gene is Adjacent to its TATA Box," *Mol. Cell Biol.*, 8(11), 4634–4641 (Nov. 1988).
S. Shoji et al., "Amino Acid Sequence of the Catalytic Subunit of Bovine Type II Adenosine Cyclic 3', 5'–Phosphate Dependent Protein Kinase," *Biochemistry*, 22(15), 3702–3709 (1983).
E.M. Southern, "Detection of Specific Sequences Among DNA Fragments Separated by Gel Electrophoresis," *J. Mol Biol.*, 98 503–517 (1975).
K. Struhl, "Nucleotide sequence and transcriptional mapping of the yeast *pet56–his3–ded1* gene region," *Nucleic Acids Res.*, 13(23), 8587–8601 (1985).
A. Tzagoloff et al., "Assembly of the Mitochondrial Membrane Systems XVI. Modified Form of the ATPase Proteolipid in Oligomycin–Resistant Mutants of *Saccharomyces cerevisiae*," *FEBS Lett.*, 65(3), 391–395 (Jun. 1976).
J. Vieira et al., "Production of Single–Stranded Plasmid DNA," *Methods Enzymol.*, 153, 3–11 (1987).
J. W. Wallis et al., "A Hyper–Recombination Mutation in *S. cerevisiae* Identifies a Novel Eukaryotic Topoisomerase," *Cell*, 58, 409–419 (Jul. 28, 1989).
M.J. Blacketer et al., "Regulation of Dimorphism in *Saccharomyces cerevisiae:* Involvement of the Novel Protein Kinase Homolog Elmlp and Protein Phosphatase 2A", *Molecular and Cellular Biology*, 13 (9), 5567–5581 (1993).

(List continued on next page.)

*Primary Examiner*—Nancy T. Vogel
*Attorney, Agent, or Firm*—Mueting, Raasch Gebhardt & Schwappach, P.A.

[57] ABSTRACT

An isolated gene and mutations thereof capable of imparting constitutive pseudohyphal growth to *S. cerevisiae* is provided. The isolated wild type gene referred to as ELM1 is also capable of coding for a novel protein kinase that determines the yeast morphology and specific physiological properties.

13 Claims, 18 Drawing Sheets

OTHER PUBLICATIONS

A.M. Myers, "Function of the Evolutionary Conserved *rho* Gene Family", Grant Application with Abstract submitted to Department of Health and Human Services (Jan. 1987).

A.M. Myers, "Analysis of A G Protein–Linked Signalling Pathway that Regulates Morphological Development in the *S. Cerevisiae* Cell Cycle", presented at the Conference on Yeast Cell Biology, Cold Spring Harbor, NY, May 13–17, 1992.

A. Myers, "Isolation of new mutations causing elongated bud phenotypes", Poster presentation at 1991 Yeast Genetics and Molecular Biology Meeting, San Francisco, CA, May 23–27, 1991, p. 88.

Jimeno et al., Science, 257:626 (1992).

A

| Plasmid | 1 kb | Complementation of elm1 |
|---|---|---|
| pA3 | (E) —P S E X— E — P — E B H E H — (H) | + |
| pA4 | (H) —————— X — P —— (E) | + |
| pA2 | (E) ——————— (H) | + |
| pA1 | (H) ——————— (E) | + |
| pE104/ST1 | (H) ——— (E) | − |
| pE104/ST3 | (H) —— (E) | − |

Fig. 3a

```
    Sau3A
  1 GATCCTTCTTGAAGTAGCTATTAAGTTGTTCGAAATGAAGTAATTATTA
101 TAGTATATAGCATGATTTTACATCACTTTAAACGTATAATTGTGAATG
201 TTTGGCCTTGAAACCCCCGATGATACTTCTTTAGGTGTTACAACTTAC
301 ATGTCACCGCGACAGCTTATACCGACATTAATTCCGAATGGCACCAT
  1  M  S  P  R  Q  L  I  P  T  L  I  P  E  W  A  P  L
401 CGCCTACGAGCCAGACACATCTTCATTGGTTCTTCTTTTTCTCAACAGAA
 35  P  T  S  Q  T  S  S  F  G  S  S  F  S  Q  Q  K
501 AATTCGACCATATGTGAAAAAAATAACTGTTAGTGACCAAGATAAGAAA
 68  I  R  P  Y  V  K  K  I  T  V  S  D  Q  D  K  K
```

AAATAGAAGTAAATCATTAAATGATGCCGCTCAACAGAGGTTATGCCAAAT

ATGAGGTAGCAACAAATAAACAATGCAACAGTCTCTAGTCCTATGAACTAA

TCGCATAGATATTATTTTTGACGCCAGGTTAACAATAATTACTTAGCATGA

TATCCCAGCAATCGTGCATAAGAGAGGATGAGTTAGATAGTCCCCCGATAA
 S  Q  Q  S  C  I  R  E  D  E  L  D  S  P  P  I

ACCAACCTATAGTACAATTATAGGAGAAAATATACACACGATCCTGGATGA
 P  T  Y  S  T  I  I  G  E  N  I  H  T  I  L  D  E

ACTATAAACCAATATACGCTAGGAGTCTCTGCAGGAAGTGGACAATTTGGT
 T  I  N  Q  Y  T  L  G  V  S  A  G  S  G  Q  F  G
                         PstI

```
 601 TATGTACGAAAAGGTACAGTTCTACTTTAGGCAAGGTTGTTGCTGTCA
 101  Y  V  R  K  A  Y  S  S  T  L  G  K  V  V  A  V  K

701 TAATGAGGCAAATCCAGCTTTGGAAGAGTAAAGGAAAAATAACGACAAA
 135  M  R  Q  I  Q  L  W  K  S  K  G  K  I  T  T  N

801 GGAAATTTTTGCGGCTTCAAGACTTCGAAATAATGTTCATATTGTGCGA
 168  E  I  F  A  A  S  R  L  R  N  N  V  H  I  V  R

1001 CATTTGCCAAAAAAATCCTGGAGGATATGACAAAAGGGTTGGAATATTT
 235  F  A  K  K  I  L  E  D  M  T  K  G  L  E  Y  L

1101 GGATGAAGAAGAAAAAGTAGCGAAACTTTCTGATTTTGGAAGTTGTATT
 268  D  E  E  E  K  V  A  K  L  S  D  F  G  S  C  I
```

Fig. 3d

```
AGATTATACCAAAAAAACCTTGGAATGCCCAGCAATATTCAGTAAATCAAG
 I  I  P  K  K  P  W  N  A  Q  Q  Y  S  V  N  Q  V

TATGAGTGGTAATGAGGCTATGAGACTTATGAATATCGAAAAATGTAGGTG
 M  S  G  N  E  A  M  R  L  M  N  I  W  K  C  R  W

CTAATAGAATGCTTGGACTCTCCTTTCAGCGAATCTATCTGGATAGTCACT
 L  I  E  C  L  D  S  P  F  S  E  S  I  W  I  V  T

GCATTCTCAGGGTTGTATTCATCGTGATATCAAACCGTCCAATATTTTATT
 H  S  Q  G  C  I  H  R  D  I  K  P  S  N  I  L  L

TTCACTCCCCAATCATTACCTTTCAGGCGATGCTAATTTTGAAGATTGTTTT
 F  T  P  Q  S  L  P  F  S  D  A  N  F  E  D  C  F
```

Fig. 3e

```
1201 CAGAGGGAATTGAACAAAATTGTTGGTACTCCGGCATTTATTGCACCAG
 301  Q  R  E  L  N  K  I  V  G  T  P  A  F  I  A  P  E

1301 AGTTGGATATTTGGTCATTGGGAGTGACACTATACTGCTTACTGTACAA
 335  L  D  I  W  S  L  G  V  T  L  Y  C  L  L  Y  N

1401 CGAAGTATCATTGAGTTCCAAAATAAATGGTAATACTTTAAACGATTTA
 368  E  V  S  L  S  S  K  I  N  G  N  T  L  N  D  L

1501 GATTTAGTAAAGGTTTTGTCGCGTGACCAGCCCCATAGATTCTAGGAATC
 401  D  L  V  K  V  L  S  R  D  Q  P  I  D  S  R  N  H

1601 TAAGAAGATTTTTGGTAGGCTACTGACTAAAAAAGGAAAGAAAAAGAC
 435  R  R  F  F  G  R  L  L  T  K  K  G  K  K  K  T
```

```
AGCTATGTCATTTGGGCAATTCCAAAGAGATTTTGTGACGGATGGCTTTA
 L  C  H  L  G  N  S  K  R  D  F  V  T  D  G  F  K
           EcoRI
CGAGCTGCCATTTTTCGGGGAAAATGAATTCGAAACCTACCACAAAATCAT
 E  L  P  F  F  G  E  N  E  F  E  T  Y  H  K  I  I
GTCATTAAAAGGTTATTGTATAAAGACGTTACTTTACGCATAAGTATTCAG
 V  I  K  R  L  L  Y  K  D  V  T  L  R  I  S  I  Q
ACAGTCAAATTTCATCGTCCAGTGTGAACCCCGTAAGAAAACGAAGGTCCTG
 S  Q  I  S  S  S  S  V  N  P  V  R  N  E  G  P  V
CTCAGGAAAAGGGAAAGACAAGGTATTGGTATCAGCAACTAGTAAAGTAAC
 S  G  K  G  K  D  K  V  L  V  S  A  T  S  K  V  T
```

Fig. 3f

1701 ACCTTCGATACATATCGACGAGGAACCGGATAAAGAATGTTTTTCGACA
 468  P   S   I   H   I   D   E   E   P   D   K   E   C   F   S   T

1801 GAGGAAGCCATTCAGGTTACGGATTTCTTAGATACTTTTTGTAGGTCAA
 501  E   E   A   I   Q   V   T   D   F   L   D   T   F   C   R   S   N

1901 TGAAAACTGACAGAAAGGCGAGTCATCCTCTCATTCGTCATTGAAAATCC
 535  K   T   D   R   K   R   V   I   L   S   F   V   I   W   N   P

2001 GGAACAGAACCCATATTAATTGCTCACAGGACAAACCGAGTTCCCCACT
     HindIII

2099 AAGCTTC

Fig. 3g

```
TCGGACCTTAGATCTTCGGCCAGAGACTCGAGGCGATTATTGTTCATCGTTAGGG
 S  D  L  R  S  S  P  D  S  S  D  Y  C  S  S  L  G

HindIII                          EcoRI
ATGAAAGCTTACCTAATTTGACTGTCAATAATGATAAGCAGAATTCGGACA
 M  K  A  Y  L  I  *  L  S  I  M  I  S  R  I  R  T
 E  S  L  P  N  L  T  V  N  N  D  K  Q  N  S  D  M CAACACCTATCAAAGCCATGATAAGAGACTAAAGAGTTCCCCTAAAGAGAACG
 N  T  Y  Q  S  H  D  K  R  L  K  S  S  P  K  R  T
 Q  H  L  S  K  P  *  *  E  T  K  E  F  P  K  E  *
 N  T  Y  Q  D  H  D  K  T  K  E  F  P  *

AATGGGATAGGACTGTTGGAAAGCGCACGGTTAATAATTCAGGGGCTAGA
```

```
              20
Elm1p    M S P R Q L I P T L I P E W A P L S Q Q S C I R E D E L D

80
Elm1p    D E I R P Y V K K I T V S D Q D K K T I N Q Y T L G V S A
Cdc28p                             M S G E L A N Y K R L E K V
cAPK (36-295)                      N T A H L D Q F E R I K T L

140
Elm1p    Q Y S V N Q V M R Q I Q L W K S K G K I T T N M S G N E A
Cdc28p   - - - - - - - - - - - - - - S E D E G V P S T A I R E I
cAPK     - - - - - - - - - - - - - - K V V K L K Q I E H T L N E K
                                                              *

200                                           220
Elm1p    S E S I W I V T N W C S L G E L Q W K R D D D E D I L P Q
Cdc28p   K R Y M E G I P K D Q P L G - - - - - - - - - - - - - -
cAPK     M F S H L R R I G R F S E P - - - - - - - - - - - - - -

260                              280
Elm1p    R D I K P S N I L L D E E E K V A K L S D F G S C I F T P
Cdc28p   R D L K P Q N L L I N K D G - N L K L G D F G - - - - - -
cAPK     R D L K P E N L L I D Q Q G - Y I Q V T D F G - - - - - -
         *   *   *                              * * *

340
Elm1p    N S K R D F V T D G F K L D I W S L G V T L Y C L L Y N E
Cdc28p   K Q Y S T - - - - - - G V D T W S I G C I F A E M C N R K
cAPK     G Y N K - - - - - - A V D W W A L G V L I Y E M A A G Y
                                     *     *

Elm1p    - - - - - - - - - - - - - - - - - - - - - - L V I K R
Cdc28p   K P S F P Q W R R K D L S Q V V P S L D P R G I D L L D K
cAPK     - - - - - - - - - - - - - - - - - - - - - - D L L R N

440
Elm1p    S V N P V R N E G P V R R F F G R L L T K K G K K K T S G

500
Elm1p    S P D S S D Y C S S L G E E A I Q V T D F L D T F C R S N

560
Elm1p    Q S H D K T K E F P end
```

400                             420
         L L E K D V T L R I S I Q D L V K V L S R D Q P I D S R N H S Q I S S S
         L L A Y D P I N R I S A R R A A I H P Y F Q E S end
         L L Q V D L T K R F G N L K D G V N D I K N H K
                    *

460                                 480
         K G K D K V L V S A T S K V T P S I H I D E E P D K E C F S T T D L R S
              520                                 540
         E S L P N L T V N N D K Q N S D M K T D R K R V I L S F V I E N P N T Y
```

CONSTITUTIVE PSEUDOHYPHAL GROWTH YEAST MUTANTS

STATEMENT OF GOVERNMENT RIGHTS

The present invention was made with the support of the National Institute of Health under Contract No. 5R29GM3925405. The Government has certain rights to this invention.

BACKGROUND OF THE INVENTION

Several fungal organisms are dimorphic, i.e., capable of existing in two forms. Such dimorphic fungi exhibit distinct morphologies in response to specific cellular signals. Typically, dimorphic fungi display either an egg-shaped, unicellular, yeast-like form, or a filamentous, mold-like form having attached and elongated cells. One example of such a dimorphism exists in the fungus *Ustilago maydis* in which haploid sporidia exhibit a yeast-like morphology. Such haploid sporidia may fuse to form an elongated dikaryon filamentous form if they bear distinct alleles at both the a and b compatibility loci. In contrast to the unicellular form, the filamentous form of *Ustilago maydis*, for example, causes corn smut.

A second well characterized example of dimorphism occurs in *Candida albicans*. This species of fungus exhibits a basic dimorphism between a budding yeast and a filamentous hyphal form. Several signals have been implicated in the switch between these two forms, including temperature, pH, nutrients, and exposure to serum factors. Mutants of *C. albicans* are known which are locked in either the yeast form or the hyphal form. Exploiting these observations for any useful purpose by classical genetic analysis is difficult, however. This is at least in part because *C. albicans* has only been observed as a diploid, and a sexual cycle has not been identified.

*Saccharomyces cerevisiae* (*S. cerevisiae*), also known as brewer's yeast or baker's yeast, also is a dimorphic species capable of displaying an egg-shaped yeast-like form and a filamentous mold-like form. Unfortunately, however, laboratory isolates of the fungus present a great variability in their ability to display this dimorphic characteristic. In this organism, nitrogen starvation in the presence of glucose is a natural inducer of the formation of the filamentous form, which is more appropriately termed pseudohyphae. See C. J. Gimeno et al., Cell, 68, 1078 (1992). Stimulation of a signal transduction pathway referred to as RAS2 facilitates this pseudohyphal response, i.e., the formation of a filamentous form.

*S. cerevisiae* pseudohyphal cells have an elongated morphology, and stay attached to each other presumably by their cell wall. Furthermore, a unipolar budding pattern occurs in which daughter cells bud, and rebud, away from their mother cell in the great majority of the cell divisions. The result is a filamentous, mold-like structure growing away from the center of the colony. Of particular note is that the pseudohyphal form of *S. cerevisiae* forage deeply into agar media, possibly as a result of degrading polysaccharides into energy producing monosaccharides. Thus, the pseudohyphal form of *S. cerevisiae* could be used in the fermentation of complex polysaccharides for the production of ethanol, for example. Unfortunately, however, the wild type *S. cerevisiae* only undergoes the pseudohyphal response in near-starvation conditions. Exploiting these observations could lead to significant utility in commercial fermentation applications.

SUMMARY

The present invention provides a genetically modified S. cerevisiae yeast strain containing a constitutive pseudohyphal growth mutant gene, wherein the yeast strain exhibits constitutive pseudohyphal growth. Also provided is a constitutive pseudohyphal growth mutant gene capable of causing constitutive pseudohyphal growth on *S. cerevisiae*. Preferably, the constitutive pseudohyphal growth mutant gene is a deletion allele elm1::URA3, an insertion allele elm1::HIS3, or a missense allele elm1-R117. The present invention also provides an isolated DNA sequence capable of controlling pseudohyphal growth in *S. cerevisiae*. The isolated DNA sequence also codes for a Ser/Thr protein kinase, which is involved in the control of pseudohyphal growth.

The present invention also provides a method of identifying constitutive pseudohyphal growth mutant genes in a yeast strain comprising: mutagenizing the yeast strain; visually identifying mutant yeast strains having elongated cells; breeding the mutant yeast strains into defined genetic backgrounds; forming a hybrid diploid strain using the mutant yeast strains having a defined genetic background; and examining the hybrid diploid strain for pseudohyphal growth characteristics. This method could be used in any of a variety of yeast strains, such as *S. cerevisiae, Ustilago maydis*, and *C. albicans*, for example. Preferably, the yeast strain is *S. cerevisiae*. Any known method can be used to mutagenize the yeast, i.e., treat the cells with a mutagenic agent. Preferably, the method used is a chemical or irradiative method. More preferably, it is a chemical method.

The present invention is also directed to a method of regulating cellular dimorphism through the use of constitutive pseudohyphal growth genes. In this way, the present invention can be used in controlling pathogenic transformation in fungi. The present invention is also directed to a method of cloning constitutive pseudohyphal growth genes using the foraging characteristic as a genetic marker.

BRIEF DESCRIPTION OF THE DRAWINGS

FIG. 3, 3a–3h Nucleotide sequence (SEQ ID NO:1) of the ELM1 locus and predicted amino acid sequence (SEQ ID NO:1) of Elm1p (protein kinase). Only the sense strand is shown. The coding region is translated below the nucleotide sequence. The location of several restriction enzyme recognition sites are indicated for comparison to FIG. 2.

FIG. 5a–5b Elm1p is homologous to Ser/Thr protein kinases. The deduced amino acid sequence of Elm1p (SEQ ID NO:1) is aligned with that of the protein kinase Cdc28p (SEQ ID NO:1) (disclosed in A. T. Locrincz et al., Nature, 307, 183–185 (1984)) and the relevant domain of the bovine cAMP dependent protein kinase catalytic subunit, α form (cAPK) (SEQ ID NO:1) (disclosed in S. Shoji et al., Biochemistry, 22, 3702–3709 (1983)). Identical residues are boxed and gaps are represented by dashes. Residues nearly invariant among protein kinases (disclosed in S. K. Hanks et al., Science, 241, 42–51 (1988)) are indicated by stars.

DETAILED DESCRIPTION OF THE INVENTION

Figure 1A:
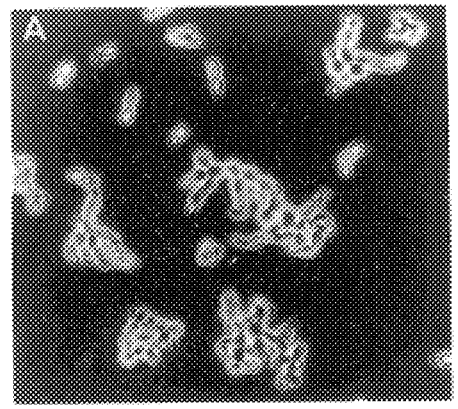
FIG. 1. Plasmid pA2 suppresses the phenotype caused by the constitutive pseudohyphal growth mutant gene elm1. Strains were cultured in SDC liquid medium supplemented according to the auxotrophic requirements. Cells were photographed while in exponential growth using a phase contrast microscope. (A): Strain α104W1, bearing elm1-1. (B): Strain A2 which was obtained by transformation of α104W1 with the suppressor plasmid pA2; uracil was omitted from the medium. (C): The A2 strain was cultured in liquid medium containing uracil, allowing plasmid loss. The culture was spread on a plate while still in the presence of uracil. About 5% of the isolated colonies displayed a mutant morphology. Furthermore, the wild type looking colonies were uracil independent, while the mutant colonies required uracil indicating they had lost the pA2 plasmid. A representative uracil dependent segregant is shown.

Saccharomyces cerevisiae (S. cerevisiae) grows either as a unicellular, egg-shaped, yeast form or as a filamentous mold-like form, which is referred to as pseudohyphae. Although the yeast form usually prevails, pseudohyphal growth may occur during nitrogen starvation in the wild type S. cerevisiae strain. A general approach has been developed that allows for the isolation of genes involved in this dimorphic transition. An isolated wild type gene, referred to herein as ELM1 (ELongated Morphology), is capable of coding for a novel protein kinase homolog, which is required for the yeast morphology.

The present invention is based on the discovery that deletion of the wild type gene ELM1 causes constitutive pseudohyphal morphology. Herein, "deletion" refers to the removal of the majority of the coding region of ELM1, or other forms of inactivation of ELM1 including: insertion of a foreign DNA sequence within its coding region; or changing a specific nucleotide sequence, such as converting the lysine codon at position 117 to an arginine codon. Furthermore, additional mutations of the wild type gene ELM1 and other specific genes, such as those referred to herein as elm1, elm2, and elm3, cause constitutive pseudohyphal growth. This is evidenced by mutant strains forming chains of connected and elongated cells that grow invasively into semisolid media, e.g., agar. It is believed that this occurs as a result of degradation of polysaccharides into energy-rich monosaccharides.

Thus, the present invention can be used in controlling pathogenic transformations in fungi. This is important in control of the prevalent human pathogen C. albicans, which can cause systemic infection when growing in the hyphal form. Such infections are frequent and life-threatening in immunosuppressed patients such as those with AIDS or undergoing chemotherapy treatment for cancer. Control of plant pathogens such as U. maydis also is possible, because prevention of the hyphal form precludes pathogenicity. Furthermore, the present invention can be used to produce yeast that can degrade polysaccharides, feasibly even cellulose, in fermentation processes. Thus, for example, bulk ethanol could be prepared from corn silage or other agricultural plant byproducts using constitutive pseudohyphal S. cerevisiae strains. Such strains could also be used for production of alcoholic beverages using various cellulose sources as the substrate for fermentation.

Constitutive pseudohyphal growth mutant genes can be obtained by chemical mutagenesis of a wild type S. cerevisiae strain, e.g., the strain containing the wild type ELM1 gene. Cells are treated with the mutagenic agent, then individual cells are separated on agar medium and allowed to form colonies. These are screened visually for the presence of elongated cells protruding from the body of the colony. Subsequent analysis of the mutant cells and their genetic properties can identify specific mutant genes that cause constitutive pseudohyphal growth.

The major characteristics imparted to yeast strains as a result of the incorporation of these mutant genes are as follows. Cells are elongated, growth occurs predominantly at the pole of the cell 180° opposite to its connection with its mother cell, and cell separation is delayed. This results in formation of expanded, branched chains of cells that grow outward from the center of a colony. These mutations are named generically elm (ELongated Morphology). Herein, a constitutive pseudohyphal growth mutant gene is referred to when this term is used in lower case letters. In contrast, the wild type gene is referred to when this term is used in upper case letters. Examples of three particularly effective mutant genes are referred to herein as elm1, elm2 and elm3.

A "constitutive pseudohyphal growth mutant gene" is used herein to refer to a gene that imparts filamentous pseudohyphal growth and polysaccharide degradation to a yeast strain in which the gene is incorporated. Preferably and advantageously the mutant genes impart constitutive pseudohyphal growth, including polysaccharide degradation, under substantially all yeast-growing conditions. Such a genetically modified yeast strain is referred to herein as a "constitutive pseudohyphal growth mutant yeast strain."

In contrast to wild type S. cerevisiae, which only converts to the pseudohyphal form in near-starvation conditions, the genetically modified form described herein undergoes filamentous, mold-like growth to form elongated cells, and polysaccharide degradation under substantially all yeast-growing conditions. That is, the pseudohyphal mutant strains can degrade polysaccharides, as evidenced by their growing into agar as opposed to growing on the surface of agar, on nitrogen-rich media, on carbon-rich media, on liquid or solid media, etc., and under all temperatures capable of effecting yeast growth (typically about 15°–37° C.). Although not intended to be limiting to the claims of the present invention, it is believed that the mutant S. cerevisiae strains described herein grow into agar media as a result of the excretion of a digestive enzyme capable of degrading polysaccharides, such as for example, a glycohydrolase.

In addition to chemical mutagenesis of the wild type S. cerevisiae strain, a constitutive pseudohyphal growth mutant yeast strain can obtained by incorporating a constitutive pseudohyphal growth mutant gene into an inbred diploid yeast strain or hybrid diploid yeast strain. Examples of inbred diploid yeast strains include, but are not limited to, ΣΣ and W303 (Table 1). Examples of hybrid diploid yeast strains include, but are not limited to, NW and ΣW (Table 1). Preferably, the mutant gene is incorporated into a hybrid diploid yeast strain. The use of hybrid diploid yeast strains imparts greater filamentous growth to the genetically altered yeast.

Strain-dependent variability in the morphology caused by the elm mutations is to be expected, considering that great variability in competence for natural pseudohyphal growth has been reported among S. cerevisiae laboratory isolated. See, for example, C. J. Gimeno, et al., Cell, 68, 1077–1090 (1992). Presumably, pseudohyphal growth is less efficient in several inbred genetic backgrounds (which are expected to be homozygous at all genetic loci), owing to specific defects in genes required for this differentiation state. These defects could become fixed in particular reference strains, since there is no selection against such mutations in the laboratory environment. Expression of the pseudohyphal state in such defective backgrounds, owing to an elm mutation, would then result in an aberrant phenotype composed of defective pseudohyphae. In hybrid diploids formed by crossing two independently maintained laboratory isolates, defects impairing pseudohyphal growth most likely are heterozygous, leading to a behavior closer to normal. Loss of ELM1 function in three different inbred diploid backgrounds can lead to three different phenotypes, with various degrees of pseudohyphal growth. In contrast, ELM1 loss in three different hybrid diploid backgrounds causes identical phenotypes, which closely resemble healthy pseudohyphal growth. Similarly, the most demonstrative pseudohyphal phenotypes caused by elm2 or elm3 are observed in hybrid backgrounds.

Pseudohyphal growth has not been reported for haploid strains of S. cerevisiae. The original elm mutants, however, are obtained by mutagenesis of an haploid strain. Although the axial budding pattern of haploids is inappropriate for pseudohyphal growth, the elm mutations always cause cell elongation even in haploid strains, allowing identification of the mutants. Several haploid elm mutants also display a unipolar budding pattern typical of diploid pseudohyphae.

The invention has been described with reference to various specific and preferred embodiments and will be further described by reference to the following detailed examples. It is understood, however, that there are many extensions, variations, and modifications on the basic theme of the present invention beyond that shown in the examples and detailed description, which are within the spirit and scope of the present invention.

EXPERIMENTAL PROCEDURES

Strains, Media and Genetic Methods

Yeast strains used in this study are described in Table 1 and were cultured at 30° C. unless specified otherwise. The following media were used: YPD (1% yeast extract, 2% peptone, 2% glucose); YPAD (YPD supplemented with 40 mg/l adenine); SD (2% glucose, 0.7% yeast nitrogen base without amino acids, supplemented as required with leucine, tryptophan, histidine, lysine, methionine, uracil and adenine at 20 mg/l each); SDC (SD supplemented with 0.5% casaminoacids in addition to the auxotrophy requirements); sporulation medium (1% potassium acetate, 0.05% glucose, 0.1% yeast extract); SLAHD (nitrogen starvation media described by C. J. Gimeno et al., Cell, 68, 1077–1090 (1992), which is incorporated herein by reference). Solid media for yeast contained 2% agar.

Standard genetic methods were used for complementation analysis, mating, and tetrad dissection as disclosed in F. Sherman et al., Methods in Yeast Genetics, Cold Spring Harbor, N.Y.: Cold Spring Harbor Laboratory, (1986), which is incorporated herein by reference. In those instances where auxotrophic markers were not available for selection of a diploid from a cross, isolated colonies of potential diploids were selected based on their increased growth rate relative to the haploids parents. In all instances diploidy was verified by the ability of the selected strains to sporulate.

TABLE 1

Strains

| Strain | Genotype | Source |
|---|---|---|
| NY13 Background: | | |
| NY13 | MATa ura3 | B. Goud et al., Cell, 53, 753–768 (1988) |
| NY180 | MATα ura3 leu2 | Obtained in an analogous manner to that disclosed in B. Goud et al. (1988) |
| aNΔelm1 | MATa ura3 elm1::URA3 | Integrative transformation of NY13 |
| NΔelm1 | MATa/MATα ura3/ura3 leu2/+ elm1::URA3/elm1::URA3 | Mating of segregants from aNΔelm1 × NY180 |
| Σ1278b Background (M. Grenson et al., Biochem, Biophys. Acta. 127, 325–338 (1966)): | | |
| MB758-5B | MATa ura3 | Siddiqui and Brandriss, Mol. Cell Biol., 8, 4634–4641 (1988) |
| MB758-6B | MATα ura3 | Obtained in an analogous manner to that disclosed in Siddiqui and Brandriss (1988) |
| MB810-3C | MATa lys2 | Obtained in an analogous manner to that disclosed in Siddiqui and Brandriss (1988) |
| MB810-5A | MATα lys2 | Obtained in an analogous manner to that disclosed in Siddiqui and Brandriss (1988) |
| ΣΣ | MATa/MATα ura3/ura3 lys2/lys2 | Mating of segregants from MB758-5B × MB810-5A |
| ΣΣΔelm1/+ | MATa/MATα ura3/ura3 lys2/lys2 elm1::URA3/+ | Integrative transformation of ΣΣ |
| aΣΔelm1 | MATa ura3 lys2 elm1::URA3 | Segregant from ΣΣΔelm1/+ |
| αΣΔelm1 | MATα ura3 lys2 elm1::URA3 | Segregant from ΣΣΔelm1/+ |
| ΣΣΔelm1 | MATa/MATα ura3/ura3 lys2/lys2 elm1::URA3/elm1::URA3 | aΣΔelm1 × αΣΔelm1 |
| W303 Background: | | |
| W303 | MATa/MATα ura3/ura3 leu2/leu2 his3/his3 trp1/trp1 ade2/ade2 | J. Wallis, Cell, 58, 409–419 (1989) |
| W303-1A | MATa ura3 leu2 his3 trp1 ade2 | Meiotic product of W303 |
| W303-1B | MATα ura3 leu2 his3 trp1 ade2 | Meiotic product of W303 |
| WWΔelm1H/+ | MATa/MATα ura3/ura3 leu2/leu2 his3/his3 trp1/trp1 ade2/ade2 elm1::HIS3/+ | Integrative transformation of W303 |
| aWΔelm1H | MATa ura3 leu2 his3 trp1 ade2 elm1::HIS3 | Segregant from WWΔelm1H/+ |
| WWΔelm1U/+ | MATa/MATα ura3/ura3 leu2/leu2 his3/his3 trp1/trp1 ade2/ade2 elm1::URA3/+ | Integrative transformation of W303 |
| aWΔelm1U | MATa ura3 leu2 his3 trp1 ade2 elm1::URA3 | Segregant from WWΔelm1U/+ |
| αWΔelm1U | MATα ura3 leu2 his3 trp1 ade2 elm1::URA3 | Segregant from WWΔelm1U/+ |
| WWΔelm1 | MATa/MATα ura3/ura3 leu2/leu2 his3/his3 trp1/trp1 ade2/ade2 elm1::URA3/elm1::HIS3 | aWΔelm1H × αWΔelm1U |
| ΔWΩ | MATa ura3 leu2 his3 trp1 ade2 ELM1ΩURA3 | Integrative transformation of W303-1A |
| αWΔcdc55 | MATα ura3 leu2 his3 trp1 ade2 cdc55::LEU2-2 | Integrative transformation of W303-1B |
| Defined Hybrid Backgrounds: | | |
| NWΔelm1 | MATa/MATα ura3/ura3 leu2/+ his3/+ trp1/+ ade2/+ elm1::URA3/elm1::URA3 | aNΔelm1 × αWΔelm1U |
| ΣWΔelm1 | MATa/MATα ura3/ura3 leu2/+ his3/+ trp1/+ ade2/+ lys2/+ elm1::URA3/elm1::URA3 | aΣelm1 × αWΔelm1U |
| NΣΔelm1 | MATa/MATα ura3/ura3 lys2/+ elm1::URA3/elm1::URA3 | aNΔelm1 × αΣΔelm1 |
| ΣWΔcdc55/+ | MATa/MATα ura3/+ leu2/+ his3/+ trp1/+ ade2/+ lys2/+ cdc55::LEU2-2/+ | MB810-3C × αWΔcdc55 |
| NW | MATa/MATα ura3/ura3 leu2/+ his3/+ trp1/+ ade2/+ | NY13 × W303-1B |
| ΣW | MATa/MATα ura3/+ leu2/+ his3/+ trp1/+ ade2/+ lys2/+ | MB810-3C × W303-1B |
| Other Backgrounds: | | |
| D273-10B/A1 | MATα met6 | A. Tzagoloff, FEBS lett., 65, 391–396 (1976) |
| E104 | MATα met6 elm1-1 | Mutagenesis of D273-10B/A1 |
| α104W1 | MATα ura3 ade2 his3 leu2 elm1-1 | Segregant from E104 × W303-1A |
| E124 | MATα met6 elm2-1 | Mutagenesis of D273-10B/A1 |
| a124W1a | MATa leu2 trp1 met6 elm2-1 | Segregant from E124 × W303-1A |
| a124W1b | MATa ade2 leu2 met6 elm2-1 | Segregant from E124 × W303-1A |

TABLE 1-continued

Strains

| Strain | Genotype | Source |
|---|---|---|
| α124Σ2 | MATα trp1 lys2 elm2-1 | Segregant from second backcross of a124W1a to Σ1278b background |
| a/αElm2 | MATa/MATα ade2/+ leu2/+ met6/+ trp1/+ lys2/+ elm2-1/elm2-1 | a124W1b × α124Σ2 |
| E130 | MATα met6 elm3-1 | Mutagenesis of D273-10B/A1 |
| a130W1a | MATα ura3 leu2 his3 elm3-1 | Segregant from E130 × W303-1A |
| a130W1b | MATa ade2 leu2 elm3-1 | Segregant from E130 × W303-1A |
| α130Σ2 | MATα ura3 lys2 elm3-1 | Segregant from second backcross of a130W1a × Σ1278b background |
| a/αElm3 | MATa/MATα ade2/+ leu2/+ met6/+ trp1/+ lys2/+ elm3-1/elm3-1 | a130W1b × α130Σ2 |

ELM1 Gene Isolation

Genes capable of restoring normal appearance, i.e., a normal morphology, to an elm1-1 mutant strain were selected from a yeast genomic library obtained from Francois Lacroute (Centre de Genetique Moleculaire du CNRS, Gif-sur-Yvette, France). The vector used, pFL38, was derived from the pUC19 bacterial vector. pFL38 contains in addition the URA3 selectable marker as well as a centromeric sequence causing maintenance at low copy number in yeast. The genomic inserts were obtained by partial Sau3A digestion (average size 3 kb) of chromosomal DNA from wild type *S. cerevisiae*, and were ligated to the BamHI site of pFL38.

The elm1-1 mutant strain (α104W1 was cultured in 100 ml of YPAD medium and transformed with 50 μg of plasmid library DNA using a scaled up version of the lithium transformation procedure, as disclosed in F. Ausubel et al., *Current Protocols in Molecular Biology*, John Wiley and Sons, NY (1989), which is incorporated herein by reference. Immediately after transformation, the cells were resuspended in 6 ml of 10 mM Tris-HCl pH 7.5, 1 mM EDTA (TE) buffer. Two ml of the cell suspension were added to each of three tubes containing 15 ml of the liquid medium SDC supplemented with histidine, leucine, tryptophan and adenine, but lacking uracil. The total number of uracil-independent transformants, $8 \times 10^4$, was estimated from a small aliquot of the TE suspension spread directly on selective dishes. The liquid cultures were incubated at 30° C. with gentle shaking for three days. An aliquot of each saturated culture (5 μl) was inoculated into 5 ml of fresh SDC medium which was again grown to saturation. The dilution procedure was repeated several times in a row, every three or four days. At various times, samples from saturated liquid cultures were also spread on selective plates and morphology of individual colonies was scored. More than 50% of the colonies from the second or third cycle of liquid cultures displayed wild type morphology. Isolated wild type colonies were selected for further analysis. As a control, the α104W1 strain was also transformed with the pFL38 vector devoid of insert. These control cells never reverted to wild type, even after five cycles of liquid cultures.

DNA Manipulations and Allele Construction

DNA manipulations were performed by standard procedures as disclosed in F. M. Ausubel, *Current Protocols in Molecular Biology*, New York: Greene Publishing Associates and Wiley-Interscience (1989); and J. Sambrook et al., *Molecular Cloning, A Laboratory Animal*, Cold Spring Harbor, N.Y.: Cold Spring Harbor Laboratory (1989), which are incorporated herein by reference. Plasmid pUC 118E is a modified version of pUC 118 in which the multiple cloning site was replaced by a unique EcoRI site. See J. Vieira et al., *Methods Enzymol.*, 153, 3–11 (1987), which is incorporated herein by reference. In each instance where a strain was constructed by gene replacement, Southern analysis (as disclosed in E. Southern, *J. Mol. Biol.*, 98, 503–517 (1975), which is incorporated herein by reference) of the transformant was performed to confirm that integration by homologous recombination had occurred as expected.

The insertion allele elm1::HIS3 was constructed as follows. The 1.4 kb EcoRI fragment of the genomic insert in pA1 was subcloned in plasmid pUC118E, resulting in plasmid pELM1/ST13. The yeast HIS3 gene (which is disclosed in K. Struhl, *Nucleic Acid Res.* 13, 8587–8601 (1985), incorporated herein by reference) was available as a 1.7 kb genomic BamHI fragment cloned in pUC118, in the orientation such that a 1.2 kb PstI fragment containing the entire HIS3 promotor and coding region could be excised. This fragment was subcloned at the unique PstI site of pELM1/ST13, present at ELM1 codon 94, forming pElm1::HIS3. A 2.6 kb EcoRI fragment from pELM1::HIS3 was used for transformation of the his3/his3 diploid strain W303 to histidine prototrophy.

The null allele elm1::URA3 was prepared as follows. The 2.8 kb genomic insert of pA 1 was excised as a SacI-SalI fragment, and subcloned in pBLUESCRIPT SK+ (Stratagene Cloning System, La Jolla, Calif.). The resultant plasmid, pELM1/ST16, was digested at the unique PstI and BglII sites, removing ELM1 codons 94 to 487. A 1.2 kb HindIII fragment of yeast DNA bearing the URA3 gene (disclosed in M. D. Rose, et al., *Gene*, 29, 113–124 (1984), which is incorporated herein by reference) was inserted in pELM1/ST16 in place of the deleted sequence. The resulting plasmid, pElm1::URA3, was digested with XbaI, generating a 2.9 kb fragment used for DNA transformation of various ura3 strains to uracil prototrophy.

The chromosomal ELM1 locus was tagged with a genetic marker as follows. The insert of the suppressing plasmid pA2 was ligated into the integrative plasmid YIp352 (disclosed in J. E. Hill et al., *Yeast*, 2, 163–167 (1986), which is incorporated herein by reference) as a 2.4 kb BamHI-SacI fragment. The resulting plasmid, pELM1ΩURA3, was linearized by digestion at its unique BglII site located within ELM1. The linearized plasmid was used to transform wild type strain W303-1A to uracil prototrophy. This type of integration results in duplication of ELM1, both copies being functional and separated from each other by the YIp352 linear plasmid which bears the URA3 marker.

The null allele cdc55::LEU2-2, similar to the cdc55::LEU2 allele described by A. M. Healy et al., *Mol.*

Cell. Biol., 11, 5767–5780 (1991), which is incorporated herein by reference, was constructed as follows. The 0.3 kb PvuII fragment from pUC119, which bears the multiple cloning region, was replaced by the 2.3 kb PvuII fragment of plasmid YCpHN (A. M. Healy et al., 1991), which bears CDC55. In the resulting plasmid, the 1.3 kb EcoRI fragment (CDC55 codons 93–526) was replaced by a BamHI linker, forming p55/ST2. A 3.0 kb BglII fragment from plasmid YEp13, containing the LEU2 gene, was inserted at the unique BamHI site of p55/ST2 resulting in pcdc55::LEU2. The 4.2 kb PvuII fragment of pcdc55::LEU2 was used to transform leu2 strains to leucine prototrophy.

Preparation of the Mutagenic Gene elm1-R117

The missense allele elm1-R117 was constructed as follows. The 1177 bp PstI-BglII fragment from pA1 was cloned in pUC119. The lysine codon AAG specifying Elm1p residue 117 was changed to the arginine codon CCG by oligonucleotide-directed site-specific mutagenesis. The nucleotide sequence of the entire PstI-BglII genomic fragment was determined to ensure no other base substitutions occurred during the mutagenesis procedure. elm1-R117 was formed by using the PstI-BglII fragment containing the lysine to arginine mutation to replace the equivalent region of the wile type ELMI sequence in plasmid pELM1/ST16. The 2.8 kb SacI-SalI fragment from the resulting plasmid was cloned in the centromeric vector pRS315 {257} to form YCpelm1. The control plasmid YCpELM1 was formed by cloning the 2.8 kb SacI-SalI fragment from pELM1/ST16 in pRS315.

The lysine residue of Elm1p position 117 is conserved in all protein kinases, and is known to be absolutely required for the catalytic mechanism of cAMP dependent protein kinase. In all instances examined, conservative substitution of this lysine by an arginine inactivated the protein kinase activity. Thus, if Elm1p codes for a protein kinase, then an arginine to lysine substitution at position 117 is expected to inactivate the catalytic activity. This mutant allele, termed elm1-R117 was constructed and introduced as part of centromeric plasmid YCpelm1 into strain aWΔelm1U, which bears the deletion allele elm1::URA3. YCpelm1 failed to restore normal cell and colony morphology to aWΔelm1U, however, the morphologic defect was corrected by control plasmid YCpELM1 (which differs from YCpelm1 only at two nucleotides within codon 117.). Thus, Lys117 is essential for activity of Elm1p.

The nucleotide sequence of elm1-R117 is identical in nucleotide sequence to ELM1 with the exception that the sequence AA at positions 649–650 is changed to the sequence CG. These substitutions result in replacement of the lysine residue at amino acid position 117 with an arginine residue (protein sequence is deduced from nucleotide sequence, and has not been confirmed directly). elm-R117 causes constitutive pseudohyphal growth.

Morphological Analyses

Colony morphology was examined using an inverted microscope, observing the cells through the gear. Higher magnifications of the cells were obtained from liquid cultures, or by resuspending cells from an agar dish in a drop of water, and examining the suspensions on a slide using phase contrast or Nomarski optics.

Nucleotide Sequence Accession Number

The nucleotide sequence of the isolated ELM1 gene has been assigned GenBank/EMBL accession number M81258. The nucleotide sequence and predicted amino acid sequence of the gene product Elm1p were analyzed and compared to the available databases using the Sequence Analysis Software Package of the Genetics Computer Group (Madison, Wis.). See, J. Devereux et al., Nucleic Acids Res., 12, 387–395 (1984) for a comprehensive set of sequence analysis programs for the VAX.

EXPERIMENTAL RESULTS

Isolation of Mutants with a Constitutive Elongated Morphology

Wild type strain D273-10B/A1 (strains used in this study are described in Table 1) was moderately mutagenized by exposure to ethyl methanesulfonate (15% survival), then plated for single colonies on YPD medium. After incubation for two to four days at 22° C., colony morphology was examined directly on the surface of the agar using an inverted microscope. Morphological mutants were identified by an irregular colony shape and the presence of elongated cells extending outward from the colony; roughly 1% of the mutagenized colonies had such a morphology. This example describes five mutants from a collection of sixty morphologically altered strains obtained by this procedure.

Each strain in the study group contains a single recessive mutation that causes cell elongation. Diploids formed by mating the mutants to reference strain W303-1A had no detectable morphologic abnormality or growth defect on YPD or SD medium. Meiotic progeny of these diploids that displayed the cell elongation phenotype (outcross progeny) were collected and backcrossed successively at least five times to the unmutagenized parent strain D273-10B/A1. The cell elongation and wild type phenotypes segregated consistently at a 2:2 ration in at least 30 tetrads, indicating that in each instance the cell elongation phenotype is a single-gene trait. In the outcross and early rounds of backcrossing considerable variation was observed in the severity of the phenotype, both in the degree of cell elongation and in the growth rate (data not shown). Decreased growth rate was observed only in morphologically abnormal progeny, and thus was a result of the same mutation that affects cell shape. In the later rounds of backcrossing, however, a uniform morphologic phenotype was observed for all progeny of each mutant, and no significant difference was detected between the growth rates of the mutant progeny and the wild type parent (data not shown). Thus, certain aspects of the phenotype caused by these mutations apparently depend on the specific genetic background.

Complementation and allelism tests determined three different genes were identified by the five morphological mutants in the study group. Complementation groups were assigned by analyzing the morphology of diploids formed in reciprocal crosses between the original mutants and their backcross progeny. Three groups were identified, two with two members each and one with a single representative (Table 2). Allelism tests were performed by observing haploid progeny from the diploids obtained in the complementation group analysis. Diploids with elongated cell morphology always produced tetrads comprising only mutant progeny (30 tetrads analyzed for each cross). Conversely, all diploids with a wild type morphology produced both mutant and wild type progeny in the ratio expected for independent assortment of unlinked genes. Thus, the three complementation groups represent three distinct gene loci, tentatively named ELM1, ELM2, and ELM3 (ELongated Morphology). Similar analysis, including allelism tests, showed ELM2 and ELM3 are distinct from five cell division cycle genes (CDC) known to cause cell elongation, namely CDC3, CDC10, CDC11, CDC12, and CDC55 (which is disclosed in L. Hartwell, Exptl. Cell Res., 69, 265–276 (1971) and A. Ilealy et al., *Mol. Cell. Biol.* 11, 5767–5780 (1971)). ELM1 was shown to be different from any of these CDC genes by its unique nucleotide sequence (see below).

TABLE 2

Complementation matrix[a]

| MATα parent | MATa parent[b] | | | | |
|---|---|---|---|---|---|
| | 104D5 | 105D5 | 102D5 | 130D5 | 156D5 |
| E104 | − | − | + | + | + |
| E105 | − | − | + | + | + |
| E102 | + | + | − | − | + |
| E130 | + | + | − | − | + |
| E156 | + | + | + | + | − |

[a]The indicated strains were mated and diploids were selected based on complementing auxotrophies. "−" indicates the diploid had a mutant morphologic phenotype, and "+" indicates the diploid had wild type or near-wild type morphology.
[b]parents are progeny of the fifth backcross to D273-10B/A1. The original mutants were outcrossed to W303-1A prior to the backcrosses. These strains all contain a leu2 auxotrophic marker; 102D5 also contains a his3 marker.

Cloning of ELM1

Figure 1B:
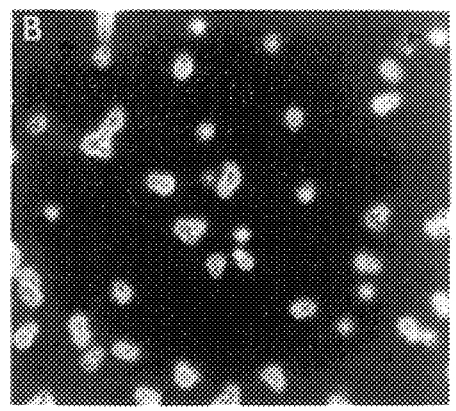

The wild type ELM1 gene was selected from a genomic library based on its ability to complement the growth defect caused by elm1-1 in strain α104W1. This strain bears the ura3 marker allowing selection of URA3 plasmids. The elm1-1 mutation of α104W1 causes elongated morphology, clumpiness, and a reduced growth rate (FIG. 1A). When DNA was stained with DAPI, a few very elongated cells seemed to bear several nuclei, suggesting that cytokinesis was impaired (data not shown). Cell viability was high despite the severely abnormal appearance of α104W1, and the phenotype was stable when the strain was maintained routinely on stock plates. A yeast genomic library based in the centromeric (low copy number) plasmid pFL38 was introduced into the α104W1 cells, and transformants were inoculated en masse in liquid medium lacking uracil. Absence of uracil from the medium maintained a selection for transforming plasmids, and growth in liquid culture presumably would allow relatively rapidly growing revertants to overtake cells still suffering from the reduced doubling time associated with the mutant phenotype. Indeed, after about 30 generations, the majority of cells in the liquid cultures displayed wild type morphology. Liquid cultures were spread on agar medium lacking uracil, and four apparently reverted yeast colonies, named A1 to A4, were further characterized (FIG. 1B shows clone A2).

Figure 1C:
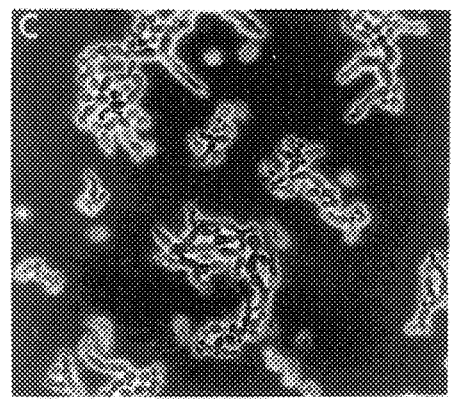
Figures 2A, 2B:
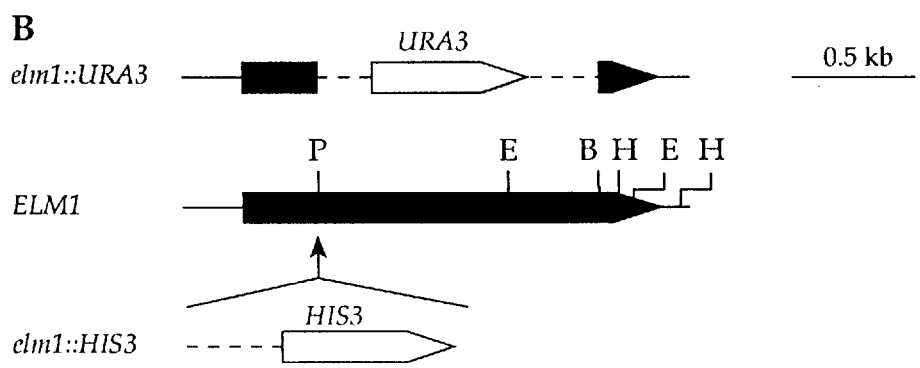
FIG. 2. Restriction Map of the ELM1 Region. (A): Delineation of a genomic region suppressing the elm1-1 phenotype. The restriction maps of inserts from several plasmids are aligned, and the suppressing ability of the corresponding plasmid is indicated. Restriction sites are shown for EcoRI, PstI, SalI, XbaI, BglII, and HindIII. Sites in parenthesis are located in the multiple cloning region of the vector. Plasmids pA1 to pA4 were selected from a genomic library, based on their ability to suppress the elm1-1 defect of strain α104W1. Inserts in pE104/ST1 and pE104/ST3 are the 1.8 kb PstI-SacI fragment and the 1.4 kb HindIII-EcoRI fragment from pA2, respectively (SacI and HindIII are located in the multiple cloning region of the vector). (B) Map of ELM1 and disrupted alleles. The region common to the inserts of pA1 to pA4 is shown in the middle diagram. The ELM1 coding sequence is marked by the solid arrow. The upper and lower diagrams show the structure of the deletion allele elm1::URA3 and the insertion allele elm1::HIS3.
Figure 3:
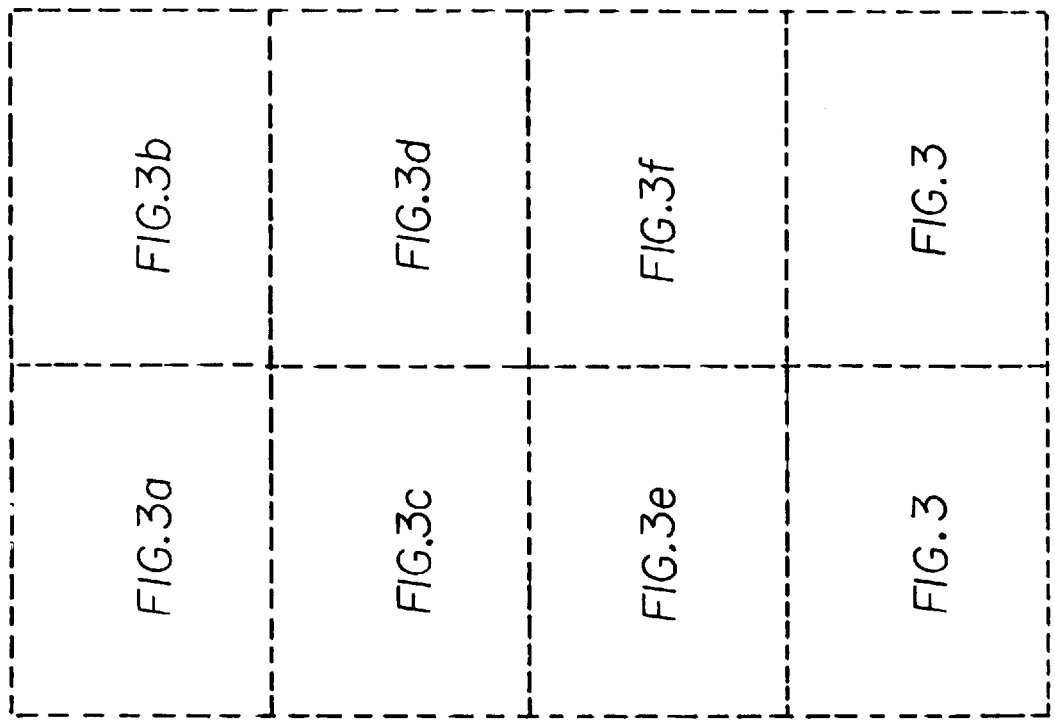
Figure 4A:
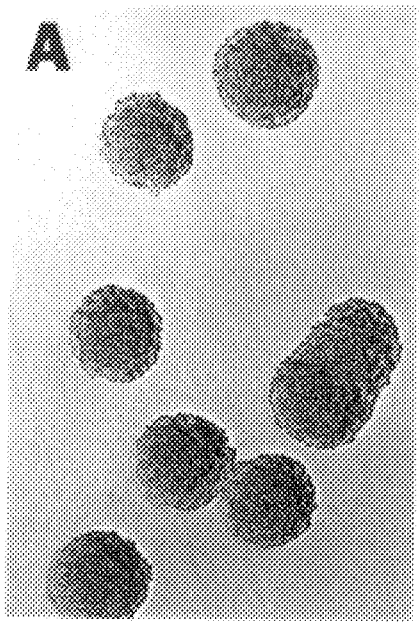
FIG. 4. The suppressor gene resides at the ELM1 locus. The suppressor locus, presumably ELM1, had been tagged by the URA3 marker in wild type strain aWΩ (see Experimental Procedures). This strain was mated with the elm1-1 strain α104W1 and meiosis was induced in the resulting diploid. Four spores from a single tetrad were separated and allowed to germinate. The resulting haploid strains were respread on YPD plates, cultured for 16 hours, then photographed in situ using an inverted microscope. Uracil requirement was also scored. This tetrad is representative of the thirty tetrads analyzed from this cross. (A) and (D): Wild type morphology, uracil independent. (B and C): Mutant morphology, uracil dependent. The mutant colonies also are representative of the original collection of mutants obtained by visual screen of the mutagenized D273-10B/A1 strain.
Figure 4B:
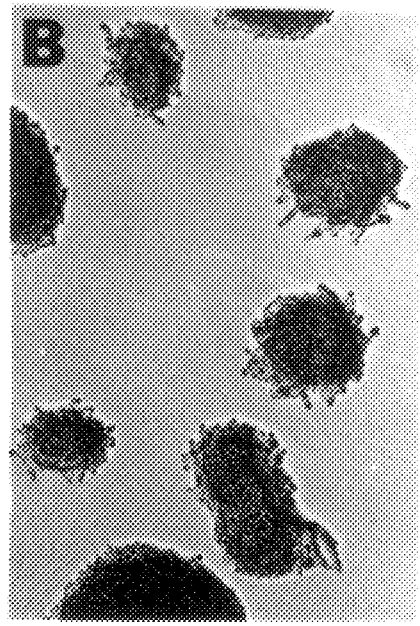
Figure 4C:
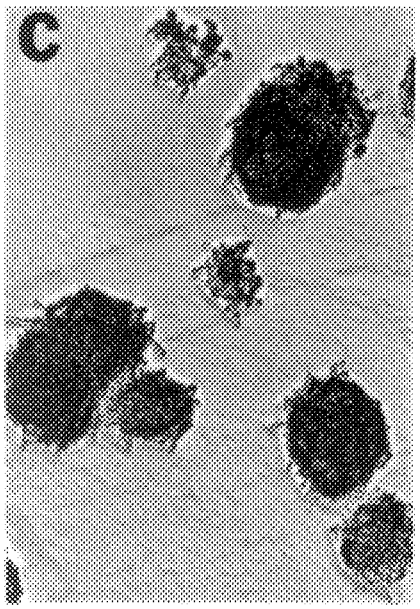
Figure 4D:
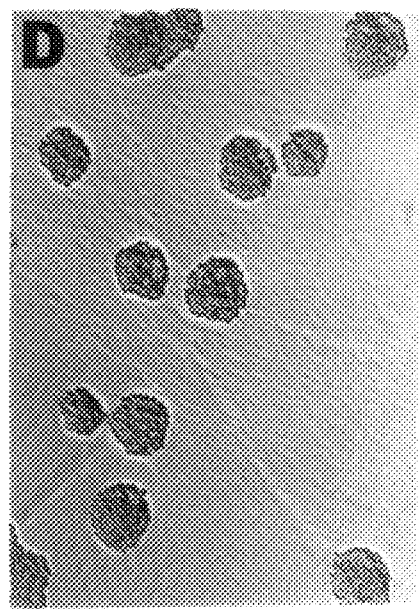

The reverted phenotype was caused by the plasmids because plasmid loss during mitosis resulted in reappearance of the mutant phenotype. FIG. 1C shows a derivative of clone A2 which presumably lost its plasmid. The four plasmids present in the reverted yeast clones were recovered, produced in *E. coli*, and named pA1 to pA4. Restriction enzyme mapping of the plasmids showed they all contain distinct genomic inserts that share an overlapping 2.1 kb sequence (FIG. 2). This common region was entirely sequenced and a single long open reading frame was observed, covering 1689 bp. Reintroducing plasmids bearing the entirety of this open reading frame into the elm1-1 strain α104W1 restored wild type morphology. Subclones containing only parts of the coding region, however, failed to restore wild type morphology (FIG. 2). Thus, this open reading frame corresponds to a yeast gene capable of suppressing the elm1-1 phenotype.

The "next door insertion" strategy, which is disclosed in R. Rothstein, *Meth. Enzymol.*, 194, 281–301 (1991), and incorporated herein by reference, indicated the cloned suppressor gene is the wild type allele of ELM1. The insert of pA2 was subcloned in the integrative plasmid YIp352. The entire plasmid was then integrated in the genome of W303-1A by homologous recombination near the suppressing locus. Thus, in the resulting strain aWΩ the suppressing locus is tagged by the URA3 marker. As expected, this strain displays wild type cell and colony morphology. The elm1-1 strain α104W1 was mated to aWΩ and meiosis was induced in the resulting heterozygous diploid. Thirty tetrads were dissected, and in every cases, two spore-derived colonies had a wild type morphology and were uracil independent, whereas two spore-derived colonies displayed obvious morphological abnormalities and were uracil dependent (FIG. 3, 3a–3h). Thus, the cloned suppressor gene marked by URA3 and the mutation elm1-1 reside at the same genetic locus.

ELM1 Codes for a Putative Novel Protein Kinase

The nucleotide sequence of ELM1 (FIG. 3, 3a–3h) (SEQ ID NO:1) revealed an open reading frame coding for 563 aminoacyl residues (FIG. 5, 5a–5b) (SEQ ID NOS:2, 3, 4). The predicted protein (Elm1p) sequence was used in a computer assisted search for related proteins. No close relative was detected, but significant homology was observed with several protein kinases. When Elm1p was compared with the available sequences of protein kinases, it appeared roughly equally diverged from all Ser/Thr kinases. FIG. 5, 5a–5b shows, as an example, Elm1p aligned with the CDC28 gene product Cdc28p (also known as p34 or histone kinase) and the catalytical region from the bovine cAMP dependent protein kinase cAPK. In this comparison, Elm1p is 23.7% identical to Cdc28p and 23.1% identical to cAPK while these two reference sequences are 23.1% identical to each other. High conservation is observed in particular regions. For example, from residue 245 to 280, Elm1p is more than 45% identical to either cAPK or Cdc28p. In addition, the 15 invariant residues found in almost every protein kinases are also conserved in Elm1p. Thus, Elm1p bears a protein kinase catalytic domain, spanning approximately residues 90 to 400. The amino and carboxy terminal regions of Elm1p, where no significant homology has been detected, may provide regulatory functions. Two subdomains have been described in protein kinases, that display different consensus sequences in enzymes specific for either tyrosine or serine/threonine. See, S. K. Hanks et al., *Science,* 241, 42–51 (1988). At this first subdomain (residues 259–264), Elm1p bears DIKPSN (SEQ ID NO:5) which fits best the Ser/Thr kinase consensus DLKPEN (SEQ ID NO:6) as opposed to the tyrosine kinase signature sequence DLAARN (SEQ ID NO:8) or DLRAAN (SEQ ID NO:7). Likewise, at the second subdomain (residues 309–317), the Elm1p sequence GTPAFIAPE (SEQ ID NO:9) matches the consensus G-T/S-X-X-F/Y-X-A-P-E (SEQ ID NO:10) for Ser/Thr specificity and is diverged from the tyrosine kinase consensus P-I/V-W-T/M-A-P-E (SEQ ID NO:110. Thus, Elm1p defines a novel branch in the Ser/Thr protein kinase family.

Inactivation of ELM1 Causes a Pseudohyphal Morphology

The W303 outcross progeny from the original E104 mutant showed an unusual variability in the severity of the elm1-1 phenotype (data not shown), even though a single mutation was known to cause the morphological defect. This suggested that the genetic background influences the elm1 phenotype. To test this hypothesis, ELM1 was inactivated directly in several laboratory strains using the gene replacement technique disclosed in R. Rothstein, *Meth. Enzymol.*, 194, 281–301 (1991), which is incorporated herein by reference, and the phenotypes were compared. Two different disrupted alleles were constructed, namely elm1::URA3 and elm1::HIS3, and were integrated by homologous recombination at the ELM1 locus of various strains. In the elm1::URA3 allele most of the ELM1 coding sequence is replaced by the URA3 gene, while ELM1 coding sequence is disrupted by HIS3 in the elm1::HIS3 allele (see FIG. 2). Replacement of ELM1 by either construct caused the same elongated morphology phenotype in haploid strains of the W303 background. Furthermore, diploids formed by mating elm1-1 strains to either elm1::URA3 or elm1::HIS3 strains also displayed the mutant phenotype, confirming that the disruptions of ELM1 are allelic with elm1-1 (data not shown).

Figure 6A:
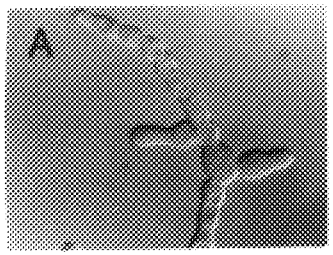
FIG. 6. Phenotype Caused by elm1 Deficiency in Inbred and Hybrid Diploid Yeast Strains. The null alleles elm1::URA3 or elm-1::HIS3 were introduced in various strains by homologous recombination, and diploids homozygous for elm1 deficiency were obtained by mating the appropriate strains. Cells were cultured for 16 hours on a YPD dish and photographed with a regular microscope equipped with Nomarski optics. (A): WWΔelm1 (W303 background). (B): NNΔelm1 (NY13 background); the insert shows the elm1 phenotype in the haploid strain aNΔelm1 (NY13 background). (C): ΣΣΔelm1 (Σ1278b background). (D): Hybrid NΣΔelm1. (E): Hybrid NWΔelm1. (F): Hybrid ΣWΔelm1. Colony morphology also was recorded in situ using an inverted microscope. (G): Hybrid ΣWΔelm1, which is also representative of ΣΣΔelm1, NN≠elm1, NΣΔelm1 and NWΔelm1 observed under the same conditions. (H): Inbred WWΔelm1 displaying some enlarged, round cells.
Figure 6B:
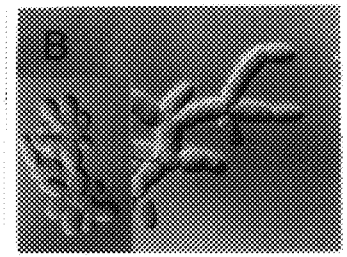
Figure 6C:
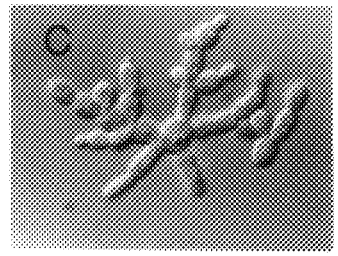

Inbred diploid strains deficient for ELM1 were obtained in the W303, NY13 and Σ1278b backgrounds (respectively WWΔelm1, NNΔelm1 and ΣΣΔelm1). All three strains presented elongated cells attached to each other, reminiscent of the elm1-1 phenotype (FIG. 6A, B, C). Strain-specific particularities were observed, however, confirming the elm1 phenotype is dependent at least in part upon the genetic background. In WWΔelm1, growth was slow, cell shape was irregular, cytokinesis was seemingly impaired and some round, enlarged cells were present (FIG. 6A, H). In contrast, NNΔelm1 strain displayed cells very regular in their elongated shape. Neither cytokinesis defects nor enlarged round cells were seen and the growth rate on plates was not significantly reduced when compared to a congenic wild type strain. During exponentional growth in liquid YPD medium, NNΔelm1 cells stayed attached presumably by their cell wall (FIG. 6B). This morphology, and in particular the budding pattern of NNΔelm1 resembles the recently described pseudohyphae of *S. cerevisiae*: chains of elongated cells which stay attached to each other, where daughter cells bud opposite to their mother, while mother cells rebud near their daughter. The result is an expanded, highly branched, mold-like structure as disclosed in C. J. Gimeno, et al., *Cell*, 68, 1077–1090 (1992). In the haploid background of NY13 the phenotype caused by elm1 deletion was similar except for the budding pattern which was axial, as expected for haploid cells. See, for example, D. Freifelder, *J. Bacteriol.*, 80, 567–568 (1960), and J. Chant et al., *Cell*, 65, 1203–1212 (1991). In this instance the elongated cells always formed buds near their mother. This resulted in small, star like clumps where each branch is composed of a single elongated cell (FIG. 6B insert). The diploid ΣΣΔelm1 strain had a phenotype close to NNΔelm1, except for less uniformity in the shape of individual cells (FIG. 6C).

Figure 6D:
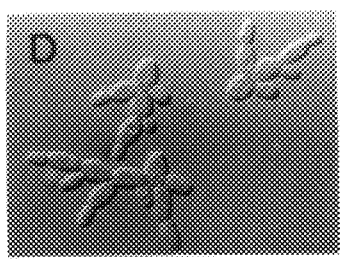
Figure 6E:
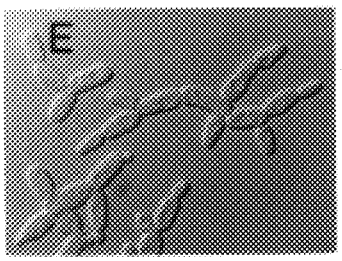
Figure 6F:
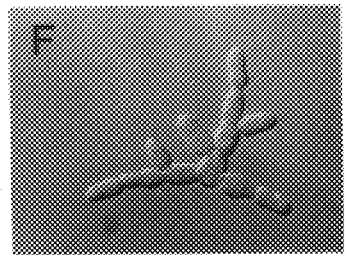
Figure 6G:
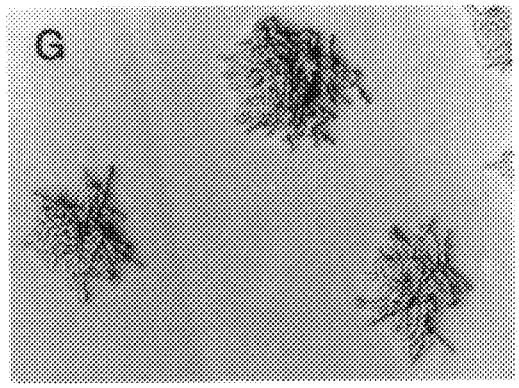
Figure 6H:
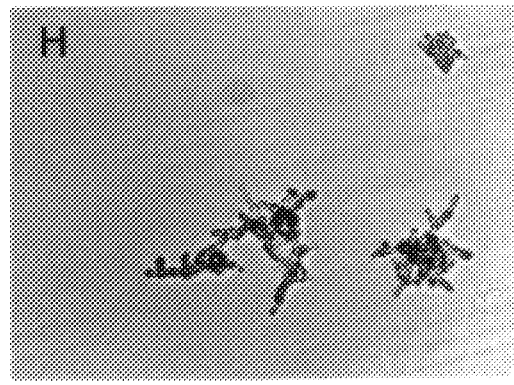
Figure 7A:
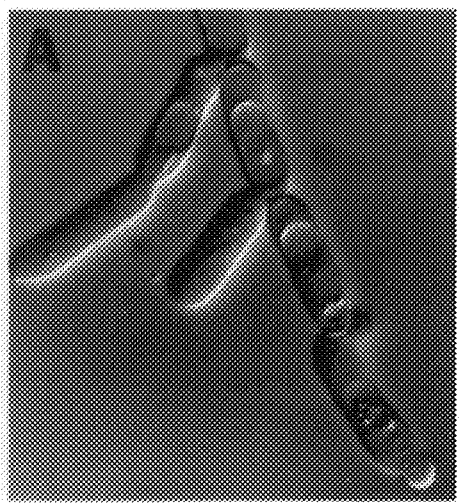
FIG. 7. The mutant genes elm2 and elm3 cause constitutive pseudohyphal growth. Diploid strains homozygous for either elm2-1 (a/αELM2) or elm3-1 (a/αElm3) were cultured on a YPD plate for 16, hours, then photographed in situ using an inverted microscope or at higher magnification with a regular microscope equipped with Nomarski optics. (A) and (B): a/αElm2. (C) and (D): a/αElm3.
Figure 7B:
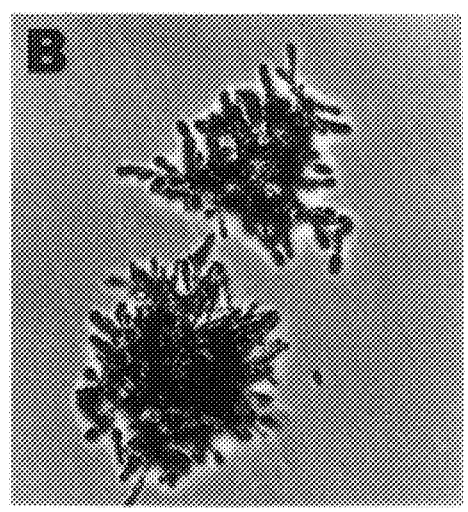
Figure 7C:
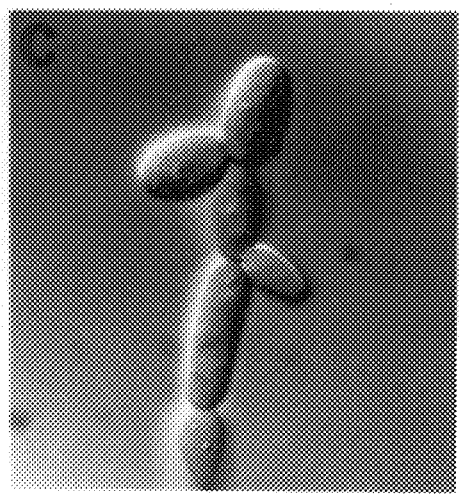
Figure 7D:
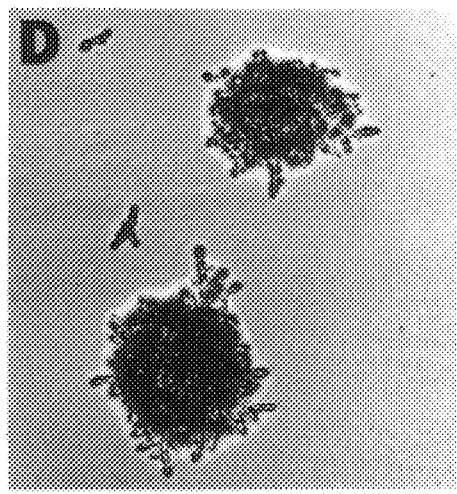

The elm1 phenotype was also analyzed in the three hybrid diploid strains (NΣΔelm1, ΣWΔelm1 and NWΔelm1) obtained by pairwise mating of haploid elm1 strains in the W303, NY13, and Σ1278b backgrounds. The phenotype of these three mutant strains was virtually identical, and resembles mostly that of NNΔelm1. Cell shape was very regular, and defective cytokinesis was not observed. Time-course examination of single cells on a plate for several generations showed the doubling time of NΣΔelm1 and ΣWΔelm1 to be approximately 1.5 hours, the same as congenic ELM1/ELM1 strains (data not shown). Cell elongation in the hybrids, however, was not as extreme as in the inbred NNΔelm1 strain. The pseudohyphal budding pattern and formation of branched structures were particularly obvious in all three elm1/elm1 hybrid diploids (FIG. 6D, E, F, G). The phenotype depicted by the hybrids, most likely represents the actual elm1 phenotype, while the inbreds probably bear some genetic defects responsible for their more or less aberrant phenotype.

elm2 and elm3 Also Cause Constitutive Pseudohyphal Growth

Many other elongated mutants obtained by mutagenesis of D273-10B/A1 behaved similarly to elm1 strains in the respect that the W303-1A outcross progeny displayed variable phenotypes, including some with pseudohyphal morphology. Strains containing elm2 or elm3 mutations were characterized further in this regard. A diploid homozygous for elm2-1, DWΣelm2-1/elm2-1, was formed in a largely hybrid background by mating a progeny clone from the outcross of the original mutant to W303-1A with one from the second backcross to Σ1278b (Table 1). Pseudohyphal characteristics including cell elongation, cell attachment (after sonication), and formation of expanded, branched chains of cells all were obvious in DWΣelm2-1/elm2-1 (FIG. 7), and the form of these cells was very similar to that of elm1 deletion mutants in F1 hybrid diploid backgrounds. Growth of single cell clones of the elm2 mutant DDelm2-2/elm2-2 was observed over time on solid YPD medium. This strain exhibited the typical extended, branched chains characteristic of pseudohyphal growth. Direct observation of clonal development showed the doubling time of DDelm2-2/elm2-2 to be essentially the same as the congenic wild type strain DD (data not shown). The same analysis was applied to the elm3 mutant DDelm3-1/elm3-1 with similar results, except for more variability in cell length (data not shown). Thus, mutations in ELM1, ELM2 or ELM3 all cause a dimorphic transition leading to a nearly identical constitutive pseudohyphal growth phenotype.

elm1, elm2 and elm3 Mutants Grow Invasively in Agar Media

A distinctive property of the previously described pseudohyphal form of *S. cerevisiae* is the ability to grow invasively under the surface of an agar medium, referred to herein as "foraging". The foraging capacity of elm1, elm2, and elm3 strains was examined by culturing patches of cells for several days on YPD plates, then scrubbing the surface of the agar with a finger under running tap water to remove the cells from the plate's surface.

Figure 8A:
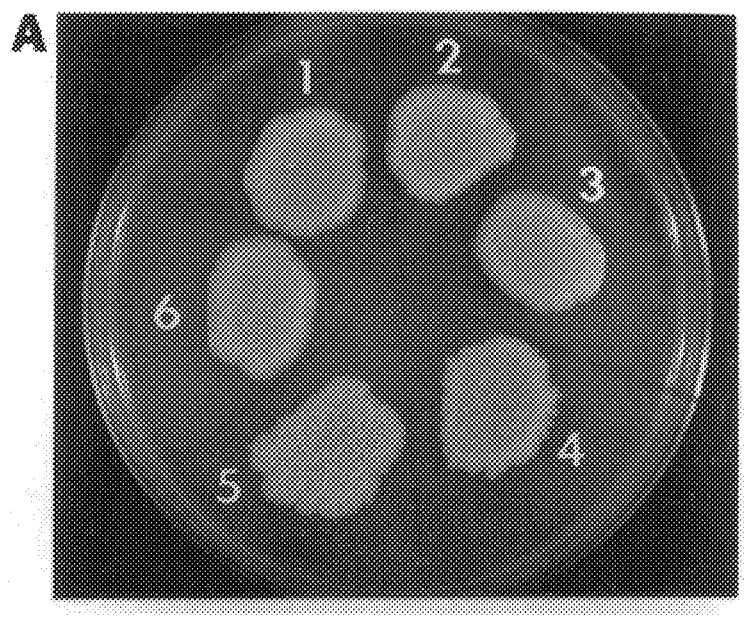
FIG. 8. Constitutive Pseudohyphae Forage Extensively in Agar Medium. (A): Diploid strains homozygous for either elm1, elm2, or elm3, as well as two wild type control strains, were cultured for four days on a YPD plate, then photographed. Strains are 1) ΣW (wild type), 2) ΣWΔelm, 3) NWΔelm, 4) a/αElm2, 5) a/αElm3, 6) NW (wild type). The elm1 strains are congenic with the wild type controls. (B): The plate was extensively washed under running tap water and photographed again. Cells invading the agar could not be washed off.
Figure 8B:
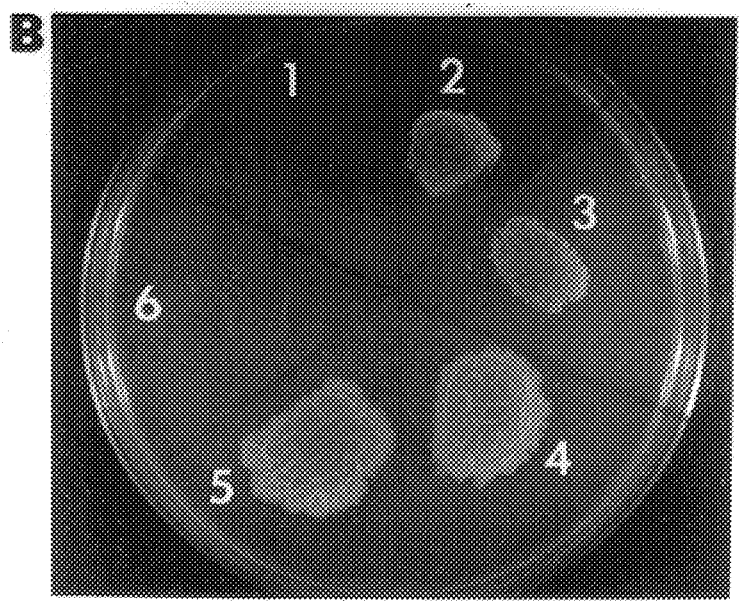
Figure 9:
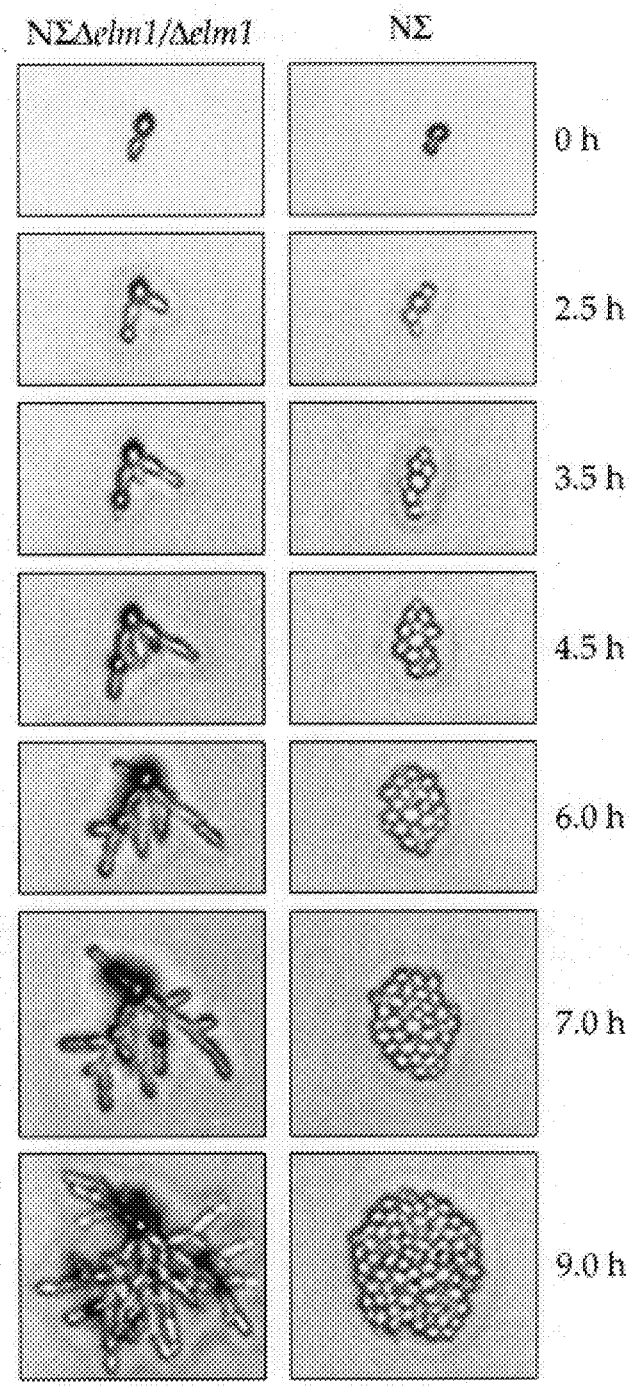
FIG. 9. Loss of ELM1 function causes constitutive pseudohyphal growth. Single cells of the indicated strains were isolated on a YPD plate using a micromanipulator, and incubated at 30° C. The developing clones were photographed at the indicated times thereafter using an inverted microscope. NΣΔelm1/elm1 is homozygous for the deletion allele elm1::URA3, whereas NΣ is homozygous for the wild type allele ELM1; otherwise the two strains are genetically identical. Both strains are F1 hybrid diploids formed by mating haploids of the NY13 and Σ1278b backgrounds.

Haploid elm2-1, elm2-2, or elm3-1 strains in the D273-10B background could not be washed from the plate, whereas the congenic wild type control strain was completely removed (FIG. 8). Observation with an inverted microscope showed most of the cells remaining after washing were located completely under the agar surface, with chains extending up to 5 cell lengths into the medium (data not shown). The ability to forage results from the elm2 or elm3 mutation, because this property consistently co-segregated with the cell elongation phenotype in at least 12 complete tetrads derived from elm2-2/ELM2 or elm3-1/ELM3 heterozygous diploids (data not shown). In the haploid D273-10B background elm1-1 and elm1-2 mutants also foraged, although to a lesser extent than the congenic elm2 or elm3 strains (data not shown). WΣΔelm1/Δelm1 and NWΔelm1/Δelm1 also exhibited obvious foraging behavior, whereas the congenic wild type control strains were completely or nearly completely removed from the YPD plate by the washing procedure (FIG. 8).

ELM2 and ELM3 Function Affects Pseudohyphal Differentiation in Response to Nitrogen Starvation.

The comprehensive phenotypic resemblance of the pseudohyphal morphologies caused either by elm1, elm2, or elm3 mutations, or by nitrogen starvation of wild type cells, suggested the mutations result in constitutive execution of the differentiation pathway that normally is triggered by nutrient availability. To test this hypothesis the effects of ELM1, ELM2, and ELM3 gene dosage on the ability of a strain to form pseudohyphae in response to nitrogen starvation were examined. Congenic diploid strains were constructed in the D273-10B background that contained either one or two functional copies of each gene to be examined. All strains displayed typical yeast-like morphology in nitrogen-rich media such as YPD or SD. On the nitrogen starvation medium SLAHD the homozygous wild type strain DD failed to display pseudohyphal growth even after 14 days on SLAHD medium, which is typical of most inbred laboratory strains. In contrast, pseudohyphal differentiation was obvious in the congenic strains DDelm2-2/+ and DDelm3-1/+ after three days on SLAHD medium. Morphologic differentiation of these two strains is dependent on the nutritional environment, because pseudohyphal cells transferred from an SLAHD plate to the nitrogen-rich medium YPD produced clones with typical yeast-like morphology; these clones again differentiated into pseudohyphae when they were replated on SLAHD. Thus, function of both ELM2 and ELM3 significantly affects the ability to flip a developmental switch in response to nitrogen starvation. This gene dosage effect was not observed for ELM1 in strain DDelm1-1/+.

STATEMENT OF AVAILABILITY

A representative example of *Saccharomyces cervisiae* E104: MATα elm1-1, was deposited on Sep. 9, 1996 with the American Type Culture Collection, Rockville, Md., 20852, and is available in accordance with the Budapest Treaty on the International Recognition of the Deposit of Microorganisms for the purpose of Patent Procedure. This deposit has been assigned ATCC No. 74388.

The disclosures of all patents, patent applications, patent documents, and publications cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
( A ) LENGTH: 2105 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

```
GATCCTTCTT  GAAGTAGCTA  TTAAGTTGTT  CGAAATGAAG  TAATTATTAA  AATAGAAGTA      60

AATCATTAAA  TGATGCCGCT  CAACAGAGGT  TATGCCAAAT  TAGTATATAG  CATGATTTTA     120

CATCACTTTA  AACGTATAAT  TTGTGAATGA  TGAGGTAGCA  ACAAATAAAC  AATGCAACAG     180

TCTCTAGTCC  TATGAACTAA  TTTGGCCTTG  AAACCCCCCG  ATGATACTTC  TTTAGGTGTT     240

ACAACTTACT  CGCATAGATA  TTATTTTTGA  CGCCAGGTTA  ACAATAATTA  CTTAGCATGA     300

ATG  TCA  CCG  CGA  CAG  CTT  ATA  CCG  ACA  TTA  ATT  CCG  GAA  TGG  GCA  CCA        348
Met  Ser  Pro  Arg  Gln  Leu  Ile  Pro  Thr  Leu  Ile  Pro  Glu  Trp  Ala  Pro
 1              5                       10                      15

TTA  TCC  CAG  CAA  TCG  TGC  ATA  AGA  GAG  GAT  GAG  TTA  GAT  AGT  CCC  CCG        396
Leu  Ser  Gln  Gln  Ser  Cys  Ile  Arg  Glu  Asp  Glu  Leu  Asp  Ser  Pro  Pro
                20                      25                      30

ATA  ACG  CCT  ACG  AGC  CAG  ACA  TCT  TCA  TTT  GGT  TCT  TCT  TTT  TCT  CAA        444
Ile  Thr  Pro  Thr  Ser  Gln  Thr  Ser  Ser  Phe  Gly  Ser  Ser  Phe  Ser  Gln
         35                      40                      45

CAG  AAA  CCA  ACC  TAT  AGT  ACA  ATT  ATA  GGA  GAA  AAT  ATA  CAC  ACG  ATC        492
Gln  Lys  Pro  Thr  Tyr  Ser  Thr  Ile  Ile  Gly  Glu  Asn  Ile  His  Thr  Ile
    50                      55                      60

CTG  GAT  GAA  ATT  CGA  CCA  TAT  GTG  AAA  AAA  ATA  ACT  GTT  AGT  GAC  CAA        540
Leu  Asp  Glu  Ile  Arg  Pro  Tyr  Val  Lys  Lys  Ile  Thr  Val  Ser  Asp  Gln
65                      70                      75                      80

GAT  AAG  AAA  ACT  ATA  AAC  CAA  TAT  ACG  CTA  GGA  GTC  TCT  GCA  GGA  AGT        588
Asp  Lys  Lys  Thr  Ile  Asn  Gln  Tyr  Thr  Leu  Gly  Val  Ser  Ala  Gly  Ser
                85                      90                      95
```

```
GGA CAA TTT GGT TAT GTA CGA AAA GCG TAC AGT TCT ACT TTA GGC AAG      636
Gly Gln Phe Gly Tyr Val Arg Lys Ala Tyr Ser Ser Thr Leu Gly Lys
            100                 105                 110

GTT GTT GCT GTC AAG ATT ATA CCA AAA AAA CCT TGG AAT GCC CAG CAA      684
Val Val Ala Val Lys Ile Ile Pro Lys Lys Pro Trp Asn Ala Gln Gln
        115                 120                 125

TAT TCA GTA AAT CAA GTA ATG AGG CAA ATC CAG CTT TGG AAG AGT AAA      732
Tyr Ser Val Asn Gln Val Met Arg Gln Ile Gln Leu Trp Lys Ser Lys
    130                 135                 140

GGA AAA ATA ACG ACA AAT ATG AGT GGT AAT GAG GCT ATG AGA CTT ATG      780
Gly Lys Ile Thr Thr Asn Met Ser Gly Asn Glu Ala Met Arg Leu Met
145                 150                 155                 160

AAT ATC GAA AAA TGT AGG TGG GAA ATT TTT GCG GCT TCA AGA CTT CGA      828
Asn Ile Glu Lys Cys Arg Trp Glu Ile Phe Ala Ala Ser Arg Leu Arg
                165                 170                 175

AAT AAT GTT CAT ATT GTG CGA CTA ATA GAA TGC TTG GAC TCT CCT TTC      876
Asn Asn Val His Ile Val Arg Leu Ile Glu Cys Leu Asp Ser Pro Phe
            180                 185                 190

AGC GAA TCT ATC TGG ATA GTC ACT AAT TGG TGC AGC CTT GGT GAA CTA      924
Ser Glu Ser Ile Trp Ile Val Thr Asn Trp Cys Ser Leu Gly Glu Leu
        195                 200                 205

CAG TGG AAA CGT GAC GAT GAT GAA GAT ATT TTA CCG CAA TGG AAA AAA      972
Gln Trp Lys Arg Asp Asp Asp Glu Asp Ile Leu Pro Gln Trp Lys Lys
    210                 215                 220

ATT GTG ATT TCA AAT TGT AGT GTT TCT ACA TTT GCC AAA AAA ATC CTG     1020
Ile Val Ile Ser Asn Cys Ser Val Ser Thr Phe Ala Lys Lys Ile Leu
225                 230                 235                 240

GAG GAT ATG ACA AAA GGG TTG GAA TAT TTG CAT TCT CAG GGT TGT ATT     1068
Glu Asp Met Thr Lys Gly Leu Glu Tyr Leu His Ser Gln Gly Cys Ile
                245                 250                 255

CAT CGT GAT ATC AAA CCG TCC AAT ATT TTA TTG GAT GAA GAA GAA AAA     1116
His Arg Asp Ile Lys Pro Ser Asn Ile Leu Leu Asp Glu Glu Glu Lys
            260                 265                 270

GTA GCG AAA CTT TCT GAT TTT GGA AGT TGT ATT TTC ACT CCC CAA TCA     1164
Val Ala Lys Leu Ser Asp Phe Gly Ser Cys Ile Phe Thr Pro Gln Ser
        275                 280                 285

TTA CCT TTC AGC GAT GCT AAT TTT GAA GAT TGT TTT CAG AGG GAA TTG     1212
Leu Pro Phe Ser Asp Ala Asn Phe Glu Asp Cys Phe Gln Arg Glu Leu
    290                 295                 300

AAC AAA ATT GTT GGT ACT CCG GCA TTT ATT GCA CCA GAG CTA TGT CAT     1260
Asn Lys Ile Val Gly Thr Pro Ala Phe Ile Ala Pro Glu Leu Cys His
305                 310                 315                 320

TTG GGC AAT TCC AAA AGA GAT TTT GTG ACG GAT GGC TTT AAG TTG GAT     1308
Leu Gly Asn Ser Lys Arg Asp Phe Val Thr Asp Gly Phe Lys Leu Asp
                325                 330                 335

ATT TGG TCA TTG GGA GTG ACA CTA TAC TGC TTA CTG TAC AAC GAG CTG     1356
Ile Trp Ser Leu Gly Val Thr Leu Tyr Cys Leu Leu Tyr Asn Glu Leu
            340                 345                 350

CCA TTT TTC GGG GAA AAT GAA TTC GAA ACC TAC CAC AAA ATC ATC GAA     1404
Pro Phe Phe Gly Glu Asn Glu Phe Glu Thr Tyr His Lys Ile Ile Glu
        355                 360                 365

GTA TCA TTG AGT TCC AAA ATA AAT GGT AAT ACT TTA AAC GAT TTA GTC     1452
Val Ser Leu Ser Ser Lys Ile Asn Gly Asn Thr Leu Asn Asp Leu Val
    370                 375                 380

ATT AAA AGG TTA TTG GAG AAA GAC GTT ACT TTA CGC ATA AGT ATT CAG     1500
Ile Lys Arg Leu Leu Glu Lys Asp Val Thr Leu Arg Ile Ser Ile Gln
385                 390                 395                 400

GAT TTA GTA AAG GTT TTG TCG CGT GAC CAG CCC ATA GAT TCT AGG AAT     1548
Asp Leu Val Lys Val Leu Ser Arg Asp Gln Pro Ile Asp Ser Arg Asn
                405                 410                 415
```

| | | | | | | | | | | | | | | | | |
|---|---|---|---|---|---|---|---|---|---|---|---|---|---|---|---|---|
| CAC | AGT | CAA | ATT | TCA | TCG | TCC | AGT | GTG | AAC | CCC | GTA | AGA | ACG | GAA | GGT | 1596 |
| His | Ser | Gln | Ile | Ser | Ser | Ser | Ser | Val | Asn | Pro | Val | Arg | Thr | Glu | Gly | |
| | | | 420 | | | | | 425 | | | | | 430 | | | |
| CCT | GTA | AGA | AGA | TTT | TTT | GGT | AGG | CTA | CTG | ACT | AAA | AAA | GGA | AAG | AAA | 1644 |
| Pro | Val | Arg | Arg | Phe | Phe | Gly | Arg | Leu | Leu | Thr | Lys | Lys | Gly | Lys | Lys | |
| | | 435 | | | | | 440 | | | | | 445 | | | | |
| AAG | ACC | TCA | GGA | AAA | GGG | AAA | GAC | AAG | GTA | TTG | GTA | TCT | GCA | ACT | AGT | 1692 |
| Lys | Thr | Ser | Gly | Lys | Gly | Lys | Asp | Lys | Val | Leu | Val | Ser | Ala | Thr | Ser | |
| | 450 | | | | | 455 | | | | | 460 | | | | | |
| AAA | GTA | ACA | CCT | TCG | ATA | CAT | ATC | GAC | GAG | GAA | CCG | GAT | AAA | GAA | TGT | 1740 |
| Lys | Val | Thr | Pro | Ser | Ile | His | Ile | Asp | Glu | Glu | Pro | Asp | Lys | Glu | Cys | |
| 465 | | | | | 470 | | | | 475 | | | | | | 480 | |
| TTT | TCG | ACT | ACG | GAC | CTT | AGA | TCT | TCG | CCA | GAC | TCG | AGC | GAT | TAT | TGT | 1788 |
| Phe | Ser | Thr | Thr | Asp | Leu | Arg | Ser | Ser | Pro | Asp | Ser | Ser | Asp | Tyr | Cys | |
| | | | | 485 | | | | | 490 | | | | | 495 | | |
| TCA | TCG | TTA | GGG | GAG | GAA | GCC | ATT | CAG | GTT | ACG | GAT | TTC | TTA | GAT | ACT | 1836 |
| Ser | Ser | Leu | Gly | Glu | Glu | Ala | Ile | Gln | Val | Thr | Asp | Phe | Leu | Asp | Thr | |
| | | | 500 | | | | | 505 | | | | | 510 | | | |
| TTT | TGT | AGG | TCA | AAT | GAA | AGC | TTA | CCT | AAT | TTG | ACT | GTC | AAT | AAT | GAT | 1884 |
| Phe | Cys | Arg | Ser | Asn | Glu | Ser | Leu | Pro | Asn | Leu | Thr | Val | Asn | Asn | Asp | |
| | | 515 | | | | | 520 | | | | | 525 | | | | |
| AAG | CAG | AAT | TCG | GAC | ATG | AAA | ACT | GAC | AGA | AAG | CGA | GTC | ATC | CTC | TCA | 1932 |
| Lys | Gln | Asn | Ser | Asp | Met | Lys | Thr | Asp | Arg | Lys | Arg | Val | Ile | Leu | Ser | |
| | 530 | | | | | 535 | | | | | 540 | | | | | |
| TTC | GTC | ATT | GAA | AAT | CCC | AAC | ACC | TAT | CAA | AGC | CAT | GAT | AAG | ACT | AAA | 1980 |
| Phe | Val | Ile | Glu | Asn | Pro | Asn | Thr | Tyr | Gln | Ser | His | Asp | Lys | Thr | Lys | |
| 545 | | | | | 550 | | | | 555 | | | | | | 560 | |
| GAG | TTC | CCC | T | AAAGAGAACG | | GGAACAGAAC | | CCATATTAAT | | TGCTCACAGG | | | | | | 2030 |
| Glu | Phe | Pro | | | | | | | | | | | | | | |

```
ACAAACCGAG   TTCCCCACTA   ATGGATAGGA   CTGTTGGAAA   GCGCACGGTT   AATAATTCAG         2090

GGGCTAGAAA   GCTTC                                                                 2105
```

( 2 ) INFORMATION FOR SEQ ID NO:2:

( i ) SEQUENCE CHARACTERISTICS:
        ( A ) LENGTH: 563 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Ser | Pro | Arg | Gln | Leu | Ile | Pro | Thr | Leu | Ile | Pro | Glu | Trp | Ala | Pro |
| 1 | | | | 5 | | | | | 10 | | | | | 15 | |
| Leu | Ser | Gln | Gln | Ser | Cys | Ile | Arg | Glu | Asp | Glu | Leu | Asp | Ser | Pro | Pro |
| | | | 20 | | | | | 25 | | | | | 30 | | |
| Ile | Thr | Pro | Thr | Ser | Gln | Thr | Ser | Ser | Phe | Gly | Ser | Ser | Phe | Ser | Gln |
| | | | 35 | | | | | 40 | | | | | 45 | | |
| Gln | Lys | Pro | Thr | Tyr | Ser | Thr | Ile | Ile | Gly | Glu | Asn | Ile | His | Thr | Ile |
| | | 50 | | | | | 55 | | | | | 60 | | | |
| Leu | Asp | Glu | Ile | Arg | Pro | Tyr | Val | Lys | Lys | Ile | Thr | Val | Ser | Asp | Gln |
| 65 | | | | | 70 | | | | | 75 | | | | | 80 |
| Asp | Lys | Lys | Thr | Ile | Asn | Gln | Tyr | Thr | Leu | Gly | Val | Ser | Ala | Gly | Ser |
| | | | | 85 | | | | | 90 | | | | | 95 | |
| Gly | Gln | Phe | Gly | Tyr | Val | Arg | Lys | Ala | Tyr | Ser | Ser | Thr | Leu | Gly | Lys |
| | | | 100 | | | | | 105 | | | | | 110 | | |
| Val | Val | Ala | Val | Lys | Ile | Ile | Pro | Lys | Lys | Pro | Trp | Asn | Ala | Gln | Gln |
| | | | 115 | | | | | 120 | | | | | 125 | | |

```
Tyr  Ser  Val  Asn  Gln  Val  Met  Arg  Gln  Ile  Gln  Leu  Trp  Lys  Ser  Lys
     130            135                      140

Gly  Lys  Ile  Thr  Thr  Asn  Met  Ser  Gly  Asn  Glu  Ala  Met  Arg  Leu  Met
145                      150                 155                           160

Asn  Ile  Glu  Lys  Cys  Arg  Trp  Glu  Ile  Phe  Ala  Ala  Ser  Arg  Leu  Arg
               165                      170                      175

Asn  Asn  Val  His  Ile  Val  Arg  Leu  Ile  Glu  Cys  Leu  Asp  Ser  Pro  Phe
               180                 185                      190

Ser  Glu  Ser  Ile  Trp  Ile  Val  Thr  Asn  Trp  Cys  Ser  Leu  Gly  Glu  Leu
          195                 200                      205

Gln  Trp  Lys  Arg  Asp  Asp  Glu  Asp  Ile  Leu  Pro  Gln  Trp  Lys  Lys
     210                 215                      220

Ile  Val  Ile  Ser  Asn  Cys  Ser  Val  Ser  Thr  Phe  Ala  Lys  Lys  Ile  Leu
225                      230                 235                           240

Glu  Asp  Met  Thr  Lys  Gly  Leu  Glu  Tyr  Leu  His  Ser  Gln  Gly  Cys  Ile
               245                      250                      255

His  Arg  Asp  Ile  Lys  Pro  Ser  Asn  Ile  Leu  Leu  Asp  Glu  Glu  Lys
               260                      265                      270

Val  Ala  Lys  Leu  Ser  Asp  Phe  Gly  Ser  Cys  Ile  Phe  Thr  Pro  Gln  Ser
          275                      280                      285

Leu  Pro  Phe  Ser  Asp  Ala  Asn  Phe  Glu  Asp  Cys  Phe  Gln  Arg  Glu  Leu
     290                      295                      300

Asn  Lys  Ile  Val  Gly  Thr  Pro  Ala  Phe  Ile  Ala  Pro  Glu  Leu  Cys  His
305                      310                      315                      320

Leu  Gly  Asn  Ser  Lys  Arg  Asp  Phe  Val  Thr  Asp  Gly  Phe  Lys  Leu  Asp
               325                      330                           335

Ile  Trp  Ser  Leu  Gly  Val  Thr  Leu  Tyr  Cys  Leu  Leu  Tyr  Asn  Glu  Leu
          340                      345                      350

Pro  Phe  Phe  Gly  Glu  Asn  Glu  Phe  Glu  Thr  Tyr  His  Lys  Ile  Ile  Glu
          355                      360                      365

Val  Ser  Leu  Ser  Ser  Lys  Ile  Asn  Gly  Asn  Thr  Leu  Asn  Asp  Leu  Val
     370                      375                      380

Ile  Lys  Arg  Leu  Leu  Glu  Lys  Asp  Val  Thr  Leu  Arg  Ile  Ser  Ile  Gln
385                      390                      395                      400

Asp  Leu  Val  Lys  Val  Leu  Ser  Arg  Asp  Gln  Pro  Ile  Asp  Ser  Arg  Asn
               405                      410                           415

His  Ser  Gln  Ile  Ser  Ser  Ser  Val  Asn  Pro  Val  Arg  Thr  Glu  Gly
               420                      425                 430

Pro  Val  Arg  Arg  Phe  Phe  Gly  Arg  Leu  Leu  Thr  Lys  Lys  Gly  Lys  Lys
          435                      440                 445

Lys  Thr  Ser  Gly  Lys  Gly  Lys  Asp  Lys  Val  Leu  Val  Ser  Ala  Thr  Ser
     450                      455                 460

Lys  Val  Thr  Pro  Ser  Ile  His  Ile  Asp  Glu  Pro  Asp  Lys  Glu  Cys
465                      470                 475                      480

Phe  Ser  Thr  Thr  Asp  Leu  Arg  Ser  Ser  Pro  Asp  Ser  Ser  Asp  Tyr  Cys
               485                      490                      495

Ser  Ser  Leu  Gly  Glu  Glu  Ala  Ile  Gln  Val  Thr  Asp  Phe  Leu  Asp  Thr
               500                      505                      510

Phe  Cys  Arg  Ser  Asn  Glu  Ser  Leu  Pro  Asn  Leu  Thr  Val  Asn  Asn  Asp
          515                      520                      525

Lys  Gln  Asn  Ser  Asp  Met  Lys  Thr  Asp  Arg  Lys  Arg  Val  Ile  Leu  Ser
     530                      535                      540

Phe  Val  Ile  Glu  Asn  Pro  Asn  Thr  Tyr  Gln  Ser  His  Asp  Lys  Thr  Lys
545                      550                      555                      560
```

Glu Phe Pro ( 2 ) INFORMATION FOR SEQ ID NO:3:

( i ) SEQUENCE CHARACTERISTICS:
        ( A ) LENGTH: 298 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
Met Ser Gly Glu Leu Ala Asn Tyr Lys Arg Leu Glu Lys Val Gly Glu
 1               5                  10                  15
Gly Thr Tyr Gly Val Val Tyr Lys Ala Leu Asp Leu Arg Pro Gly Gln
             20                  25                  30
Gly Gln Arg Val Val Ala Leu Lys Lys Ile Arg Leu Glu Ser Glu Asp
         35                  40                  45
Glu Gly Val Pro Ser Thr Ala Ile Arg Glu Ile Ser Leu Leu Lys Glu
     50                  55                  60
Leu Lys Asp Asp Asn Ile Val Arg Leu Tyr Asp Ile Val His Ser Asp
 65                  70                  75                  80
Ala His Lys Leu Tyr Leu Val Phe Glu Phe Leu Asp Leu Asp Leu Lys
                 85                  90                  95
Arg Tyr Met Glu Gly Ile Pro Lys Asp Gln Pro Leu Gly Ala Asp Ile
             100                 105                 110
Val Lys Lys Phe Met Met Gln Leu Cys Lys Gly Ile Ala Tyr Cys His
         115                 120                 125
Ser His Arg Ile Leu His Arg Asp Leu Lys Pro Gln Asn Leu Leu Ile
     130                 135                 140
Asn Lys Asp Gly Asn Leu Lys Leu Gly Asp Phe Gly Leu Ala Arg Ala
145                 150                 155                 160
Phe Gly Val Pro Leu Arg Ala Tyr Thr His Glu Ile Val Thr Leu Trp
                 165                 170                 175
Tyr Arg Ala Pro Glu Val Leu Leu Gly Lys Gln Tyr Ser Thr Gly
             180                 185                 190
Val Asp Thr Trp Ser Ile Gly Cys Ile Phe Ala Glu Met Cys Asn Arg
         195                 200                 205
Lys Pro Ile Phe Ser Gly Asp Ser Glu Ile Asp Gln Ile Phe Lys Ile
     210                 215                 220
Phe Arg Val Leu Gly Thr Pro Asn Glu Ala Ile Trp Pro Asp Ile Val
225                 230                 235                 240
Tyr Leu Pro Asp Phe Lys Pro Ser Phe Pro Gln Trp Arg Arg Lys Asp
                 245                 250                 255
Leu Ser Gln Val Val Pro Ser Leu Asp Pro Arg Gly Ile Asp Leu Leu
             260                 265                 270
Asp Lys Leu Leu Ala Tyr Asp Pro Ile Asn Arg Ile Ser Ala Arg Arg
         275                 280                 285
Ala Ala Ile His Pro Tyr Phe Gln Glu Ser
         290                 295
```

( 2 ) INFORMATION FOR SEQ ID NO:4:

( i ) SEQUENCE CHARACTERISTICS:
        ( A ) LENGTH: 260 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Asn | Thr | Ala | His | Leu | Asp | Gln | Phe | Glu | Arg | Ile | Lys | Thr | Leu | Gly | Thr |
|---|---|---|---|---|---|---|---|---|---|---|---|---|---|---|---|
| 1 | | | | 5 | | | | | 10 | | | | | 15 | |

| Gly | Ser | Phe | Gly | Arg | Val | Met | Leu | Val | Lys | His | Met | Glu | Thr | Gly | Asn |
| | | | 20 | | | | 25 | | | | | 30 | | | |

| His | Tyr | Ala | Met | Lys | Ile | Leu | Asp | Lys | Gln | Lys | Val | Val | Lys | Leu | Lys |
| | | 35 | | | | | 40 | | | | | 45 | | | |

| Gln | Ile | Glu | His | Thr | Leu | Asn | Glu | Lys | Arg | Ile | Leu | Gln | Ala | Val | Asn |
| | 50 | | | | | 55 | | | | | 60 | | | | |

| Phe | Pro | Phe | Leu | Val | Lys | Leu | Glu | Phe | Ser | Phe | Lys | Asp | Asn | Ser | Asn |
| 65 | | | | | 70 | | | | 75 | | | | | | 80 |

| Leu | Tyr | Met | Val | Met | Glu | Tyr | Val | Pro | Gly | Gly | Glu | Met | Phe | Ser | His |
| | | | | 85 | | | | | 90 | | | | | 95 | |

| Leu | Arg | Arg | Ile | Gly | Arg | Phe | Ser | Glu | Pro | His | Ala | Arg | Phe | Tyr | Ala |
| | | | 100 | | | | | 105 | | | | | 110 | | |

| Ala | Gln | Ile | Val | Leu | Thr | Phe | Glu | Tyr | Leu | His | Ser | Leu | Asp | Leu | Ile |
| | | 115 | | | | | 120 | | | | | 125 | | | |

| Tyr | Arg | Asp | Leu | Lys | Pro | Glu | Asn | Leu | Leu | Ile | Asp | Gln | Gln | Gly | Tyr |
| | 130 | | | | | 135 | | | | | 140 | | | | |

| Ile | Gln | Val | Thr | Asp | Phe | Gly | Phe | Ala | Lys | Arg | Val | Lys | Gly | Arg | Thr |
| 145 | | | | | 150 | | | | | 155 | | | | | 160 |

| Trp | Thr | Leu | Cys | Gly | Thr | Pro | Glu | Tyr | Leu | Ala | Pro | Glu | Ile | Ile | Leu |
| | | | | 165 | | | | | 170 | | | | | 175 | |

| Ser | Lys | Gly | Tyr | Asn | Lys | Ala | Val | Asp | Trp | Trp | Ala | Leu | Gly | Val | Leu |
| | | | 180 | | | | | 185 | | | | | 190 | | |

| Ile | Tyr | Glu | Met | Ala | Ala | Gly | Tyr | Pro | Pro | Phe | Phe | Ala | Asp | Gln | Pro |
| | | 195 | | | | | 200 | | | | | 205 | | | |

| Ile | Gln | Ile | Tyr | Glu | Lys | Ile | Val | Ser | Gly | Lys | Val | Arg | Phe | Pro | Ser |
| | 210 | | | | | 215 | | | | | 220 | | | | |

| His | Phe | Ser | Ser | Asp | Leu | Lys | Asp | Leu | Leu | Arg | Asn | Leu | Leu | Gln | Val |
| 225 | | | | | 230 | | | | | 235 | | | | | 240 |

| Asp | Leu | Thr | Lys | Arg | Phe | Gly | Asn | Leu | Lys | Asp | Gly | Val | Asn | Asp | Ile |
| | | | | 245 | | | | | 250 | | | | | 255 | |

| Lys | Asn | His | Lys |
| | | | 260 |

( 2 ) INFORMATION FOR SEQ ID NO:5:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

| Asp | Ile | Lys | Pro | Ser | Asn |
|---|---|---|---|---|---|
| 1 | | | | 5 | |

( 2 ) INFORMATION FOR SEQ ID NO:6:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

Asp Leu Lys Pro Glu Asn
1               5

( 2 ) INFORMATION FOR SEQ ID NO:7:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: protein ( x i ) SEQUENCE DESCRIPTION: SEQ ID NO:7:

Asp Leu Ala Ala Arg Asn
1               5

( 2 ) INFORMATION FOR SEQ ID NO:8:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: protein ( x i ) SEQUENCE DESCRIPTION: SEQ ID NO:8:

Asp Leu Arg Ala Ala Asn
1               5

( 2 ) INFORMATION FOR SEQ ID NO:9:

( i ) SEQUENCE CHARACTERISTICS:
    ( A ) LENGTH: 9 amino acids
    ( B ) TYPE: amino acid
    ( D ) TOPOLOGY: linear ( i i ) MOLECULE TYPE: protein ( x i ) SEQUENCE DESCRIPTION: SEQ ID NO:9:

Gly Thr Pro Ala Phe Ile Ala Pro Glu
1               5

( 2 ) INFORMATION FOR SEQ ID NO:10:

( i ) SEQUENCE CHARACTERISTICS:
    ( A ) LENGTH: 9 amino acids
    ( B ) TYPE: amino acid
    ( D ) TOPOLOGY: linear ( i i ) MOLECULE TYPE: protein ( x i ) SEQUENCE DESCRIPTION: SEQ ID NO:10:

Gly Xaa Xaa Xaa Xaa Xaa Ala Pro Glu
1               5

( 2 ) INFORMATION FOR SEQ ID NO:11:

( i ) SEQUENCE CHARACTERISTICS:
    ( A ) LENGTH: 7 amino acids
    ( B ) TYPE: amino acid
    ( D ) TOPOLOGY: linear ( i i ) MOLECULE TYPE: protein ( x i ) SEQUENCE DESCRIPTION: SEQ ID NO:11:

Pro Xaa Trp Xaa Ala Pro Glu
1               5

What is claimed is:

1. A genetically modified *S. cerevisiae* yeast strain containing a ELM1 mutant gene in a genetic background selected from the group consisting of W303, NY13, Σ1278b, and combinations thereof.

2. The genetically modified *S. cerevisiae* yeast strain of claim 1 wherein the ELM1 mutant gene is a deletion allele.

3. The genetically modified *S. cerevisiae* yeast strain of claim 2 wherein the deletion allele is elm1::HIS3.

4. The genetically modified *S. cerevisiae* yeast strain of claim 1 wherein the ELM1 mutant gene is an insertion allele.

5. The genetically modified *S. cerevisiae* yeast strain of claim 4 wherein the insertion allele is elm1::HIS3.

6. The genetically modified *S. cerevisiae* yeast strain of claim 1 wherein the ELM1 mutant gene is a missense allele.

7. The genetically modified *S. cerevisiae* yeast strain of claim 6 wherein the missense allele is elm1::R117.

8. The genetically modified *S. cerevisiae* yeast strain of claim 1 which is a diploid yeast strain.

9. The genetically modified *S. cerevisiae* yeast strain of claim 8 wherein the diploid yeast strain is a hybrid diploid yeast strain.

10. The genetically modified *S. cerevisiae* yeast strain of claim 9 wherein the hybrid diploid yeast strain is selected from the group consisting of NWΔelm1, ΣWΔelm1, and NΣΔelm1.

11. The genetically modified S. cerevisiae yeast strain of claim 1 wherein the diploid yeast strain is an inbred diploid yeast strain.

12. The genetically modified *S. cerevisiae* yeast strain of claim 11 wherein the inbred diploid yeast strain is selected from the group consisting of WWΔelm 1, ΣΣΔelm1, and NNΔelm1.

13. A genetically modified *S. cerevisiae* yeast strain selected from the group consisting of NWΔelm1, ΣWΔelm1, and NΣΔelm1, WWΔelm1, ΣΣΔelm1, NNΔelm1, a/αElm2, and a/αElm3.

* * * * *

UNITED STATES PATENT AND TRADEMARK OFFICE
CERTIFICATE OF CORRECTION

PATENT NO.    : 5,858,765
DATED         : January 12, 1999
INVENTOR(S)   : Myers et al.

It is certified that error appears in the above-identified patent and that said Letters Patent is hereby corrected as shown below:

Title page,
Item "[21] Appln. No.:", delete "61,636", and insert -- 08/061,636 --;

Column 9,
Line 31, delete "(";

Claim 3,
Line 2, delete "HIS3", and insert -- URA3 --; and

Claim 11,
Line 1, delete "1", and insert -- 8 --.

Signed and Sealed this

Fourteenth Day of August, 2001

*Attest:*

NICHOLAS P. GODICI
*Attesting Officer*    Acting Director of the United States Patent and Trademark Office